US008071815B2

(12) United States Patent
Indra et al.

(10) Patent No.: US 8,071,815 B2
(45) Date of Patent: Dec. 6, 2011

(54) CTIP2 EXPRESSION IN SQUAMOUS CELL CARCINOMA

(76) Inventors: Arup Kumar Indra, Corvallis, OR (US); Gitali Indra, Corvallis, OR (US); Joseph Abecassis, Strasbourg (FR); Mark Leid, Corvallis, OR (US)

( * ) Notice: Subject to any disclaimer, the term of this patent is extended or adjusted under 35 U.S.C. 154(b) by 126 days.

(21) Appl. No.: 12/505,437

(22) Filed: Jul. 17, 2009

(65) Prior Publication Data

US 2010/0015625 A1    Jan. 21, 2010

Related U.S. Application Data

(60) Provisional application No. 61/081,667, filed on Jul. 17, 2008, provisional application No. 61/173,111, filed on Apr. 27, 2009.

(51) Int. Cl.
*C12Q 1/68* (2006.01)

(52) U.S. Cl. .............. 568/6; 435/7.1; 435/7.23; 436/64; 436/501; 530/350; 530/387.7; 530/388.8; 530/389.7; 536/23.5

(58) Field of Classification Search ............... 435/6, 7.1, 435/7.23; 530/350, 387.7, 388.8, 389.7; 536/23.5; 436/64, 501
See application file for complete search history.

(56) References Cited

U.S. PATENT DOCUMENTS 5,683,885 A   11/1997  Kieback
5,849,477 A   12/1998  O'Mally et al.

FOREIGN PATENT DOCUMENTS

WO    WO 2008/006363 A2   1/2008

OTHER PUBLICATIONS

Abe et al., "Nucleolar organizer regions as a marker of growth rate in squamous cell carcinoma of the lung," *Thorax*, 47:778-780 (1992).
Avram et al., "COUP-TF (chicken ovalbumin upstream promoter transcription factor)-interacting protein 1 (CTIP1) is a sequence-specific DNA binding protein," *Biochem. J.*, 368:555-563 (2002).
Avram et al., "Isolation of a Novel Family of C2H2 Zinc Finger Proteins Implicated in Transcriptional Repression Mediated by Chicken Ovalbumin Upstream Promoter Transcription Factor (COUP-TF) Orphan Nuclear Receptors," *The Journal of Biological Chemistry*, 275(1):10315-10322 (Apr. 7, 2000).
Davelaar et al., "A combination of serum tumor markers identifies high-risk patients with early-stage squamous cervical cancer," Abstract, *Tumour Biol.*, 29(1):9-17 (2008).
Ganguli-Indra et al., "CTIP2 Expression in Human Head and Neck Squamous Cell Carcinoma is Linked to Poorly Differentiated Tumor Status," *PLoS ONE*, 4(4):e5367 1-10 (Apr. 2009).

Golonzhka et al., Expression of COUP-TF-interacting protein 2 (CTIP2) in mouse skin during development and in adulthood, *Gene Expr Patterns*, 7(7):754-760 (Aug. 2007).
Grenier et al., "Differential immunohistochemical and biological profile of squamous cell carcinoma of the breast," Abstract, *Anticancer Res.*, 27(1B):547-55 (Jan.-Feb. 2007 ).
Indra et al., "TAF10 is required for the establishment of skin barrier function in foetal, but not in adult mouse epidermis," *Developmental Biology*, 285:28-37 (2005).
Jemal et al., "Cancer Statistics," *CA Cancer J Clin*, 55:10-30 (2005).
Jemal et al., "Cancer Statistics," *CA Cancer J Clin*, 58:71-96 (2008).
Koker and Kleer, "p63 Expression in Breast Cancer: A Highly Sensitive and Specific Marker of Metaplastic Carcinoma," *The American Journal of Surgical Pathology*, 28(11):1506-1512 (Nov. 2004).
Li et al., "Salivary Transcriptome Diagnostics for Oral Cancer Detection," *Clinical Cancer Research*, 10:8442-8450 (Dec. 15, 2004).
Marur and Foratiere, "Head and Neck Cancer: Changing Epidemiology, Diagnosis, and Treatment," *Mayo Clin Proc.*, 83(4):489-501 (2008).
Megha et al., "Primary squamous cell carcinoma of the breast: a case report," Abstract, *Pathologica*, 96(2):45-8 (Apr. 2004).
Mori et al., "Preoperative diagnosis of malignant transformation arising from mature cystic teratoma of the ovary," Abstract, *Gynecol Oncol.*, 90(2):338-41 (2003).
Niho and Shinkai, "Tumor markers in lung cancer," Abstract, *Gan To Kagaku Ryoho.*, 28(13):2089-2093 (Dec. 2001).
Nowak et al, "BMI1 is a target gene of E2F-1 and is strongly expressed in primary neuroblastomas," *Nucleic Acids Research*, 34(6):1745-1754 (2006).
Patel et al., "New Approaches To the Understanding of the Molecular Basis of Oral Cancer," *Crit. Rev. Oral Biol. Med.*, 12:55-63 (2001).
Riggs et al., "Decreased Chicken Ovalbumin Upstream Promoter Transcription Factor II Expression in Tamoxifen-Resistant Breast Cancer Cells," *Cancer Research*, 66(20):10188-10198 (2006).
Suzuki et al., "Clinical significance of combined use of macrophage colony-stimulating factor and squamous cell carcinoma antigen as a selective diagnostic marker for squamous cell carcinoma arising in mature cystic teratoma of the ovary," Abstract, *Gynecol Oncol.*, 77(3):405-409 (Jun. 2000).
Tas et al., "Utility of the serum tumor markers: CYFRA 21.1, carcinoembryonic antigen (CEA), and squamous cell carcinoma antigen (SCC) in squamous cell lung cancer," Abstract, *J Exp Clin Cancer Res.*, 19(4):477-81 (Dec. 2000).
Topark-Ngarm et al., "CTIP2 Associates with the NuRD Complex on the Promoter of p57KIP2, a Newly Identified CTIP2 Target Gene," *The Journal of Biological Chemistry*, 281(43):32272-32283 (Oct. 27, 2006).

*Primary Examiner* — Stephen Rawlings
(74) *Attorney, Agent, or Firm* — Klarquist Sparkman, LLP

(57) ABSTRACT

The present disclosure provides methods of diagnosing and staging squamous cell carcinomas, for instance head and neck (HNSCC), by detecting chicken ovalbumin upstream promoter-transcription factor-interacting protein 2 (CTIP2) expression. For example, it is demonstrated herein that expression of CTIP2 is increased in SCC relative to a corresponding normal sample. Also included are kits for detecting SCC, as well as methods for identifying CTIP2 inhibitors.

8 Claims, 10 Drawing Sheets

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligo Nucleotide Primer

<400> SEQUENCE: 1
atctgtccca agcaggagaa                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligo Nucleotide Primer

<400> SEQUENCE: 2
gtctgaccct caccctgagt                                              20

<210> SEQ ID NO 3
<211> LENGTH: 21
<212> TYPE: DNA
<213> ORGANISM: Artificial Sequence
```

```
<220> FEATURE:
<223> OTHER INFORMATION: Synthetic Oligo Nucleotide Primer

<400> SEQUENCE: 3
agcaggagaa cattgcaggt a                                               21

<210> SEQ ID NO 4
<211> LENGTH: 21
<212> TYPE: DNA
<213> ORGANISM: Artificial Sequence
<220> FEATURE:
<223> OTHER INFORMATION: Synthetic Oligo Nucleotide Primer

<400> SEQUENCE: 4
ggaaattcat gagcggggac t                                               21
```

CTIP2 EXPRESSION IN SQUAMOUS CELL CARCINOMA

CROSS-REFERENCE TO RELATED APPLICATIONS

This application claims the benefit of U.S. Provisional Patent Application No. 61/081,667 filed Jul. 17, 2008, and U.S. Provisional Patent Application No. 61/173,111 filed Apr. 27, 2009, both of which are incorporated by reference in their entirety.

FIELD OF THE DISCLOSURE

This application relates to methods of diagnosing and staging cancer, for instance squamous cell carcinoma, by detecting chicken ovalbumin upstream promoter-transcription factor-interacting protein 2 (CTIP2) expression.

BACKGROUND

Squamous cell carcinoma (SCC) is a form of cancer that occurs in many different organs, including the skin, lips, mouth, esophagus, head and neck, urinary bladder, prostate, lungs, breast, vagina, cervix, and ovaries. It is a malignant tumor of the squamous epithelium. Squamous cell carcinomas may be located in situ (confined to the original site) or invasive. Squamous cell carcinomas in situ are also called Bowen's disease. In contrast to other epithelial carcinomas such as basal cell carcinomas, squamous cell carcinomas have a greater risk for metastasis and thus early diagnosis is important in the effective treatment of SCC.

Breast cancer and cervical cancer are the most common forms of cancer in women. Primary breast or cervical squamous cell carcinomas are rare; however, when they do occur they are associated with high mortality rates due to the aggressive nature of these cancers (Aparicio et al., *Eur J Obstet Gynecol Reprod Biol.*, 137(2):222-6, 2008). Primary ovarian squamous cell carcinoma also occurs infrequently, and is difficult to detect preoperatively. Given the issues related to ovarian SCC diagnosis, most patients are not affirmatively diagnosed until the disease is advanced, which in turn increases the mortality rate of this form of cancer in women to about 58% in the United States.

In men, primary prostate cancer accounts for less than 1% of all prostate cancer cases and is associated with poor prognosis. The introduction of a serum-based test to detect Prostate Specific Antigen (PSA) led to a marked increase in the number of ambiguous test samples. Accordingly, additionally pathological study of these samples is necessary to positively identify a primary prostate squamous cell carcinoma sample.

Many of the primary SCCs rely on a combination of pathological findings, adjuvant treatments such as radiation, surgery or chemotherapy, and/or the presence or absence of multiple serum markers to aid in the diagnosis of a primary SSCs (Suzuki et al., *Gynecol. Oncol.*, 77(3):405-9, 2000; Tas et al., *J. Exp. Clin. Cancer Res.*, 19(4):477-81, 2000; Megha et al., *Pathologica.*, 96(2):45-8, 2004).

Head and neck squamous cell carcinoma (HNSCC) is the sixth most common cancer in the world and is a major cause of significant morbidity. In the United States, HNSCC accounts for over 90% of all head and neck cancers. It is estimated that 35,310 new cases will be diagnosed and that 7,500 deaths will result from HNSCC in the United States in 2008 (Jemal et al., (2008) *CA Cancer J Clin,* 58:71-96; Marur (2008) *Mayo Clinic proceedings* 83:489-501). Patients with HNSCC have a 60% mortality rate even with standard therapy such as radiation, surgery and/or chemotherapy. HNSCC has been linked to tobacco and betel nut use, alcohol consumption, frequent mouthwash use, and exposure to human papillomavirus (HPV), and individuals having a long-standing history of smoking and alcohol use are at the greatest risk for developing HNSCC (Marur (2008) *Mayo Clinic proceedings* 83:489-501; Spitz (1994) *Seminars in Oncology* 21:281-288).

New approaches in the treatment of advanced HNSCC include chemotherapy and surgical treatments that are designed to achieve organ preservation and to improve overall survival (Forastiere, et al., (2001) *The New England Journal of Medicine,* 345:1890-1900). Disappointingly, although these treatments enhance quality of life and moderate pain, survival rates have not improved for this type of cancer (Jemal, et al., (2005) *CA Cancer J Clin* 55:10-30; Patel (2001) *Crit. Rev Oral Biol Med* 12:55-63). There has been no significant improvement in 5-year survival over the past 20 years, despite aggressive and multidisciplinary treatment approaches (Friedlander (2003) *Arch Otolaryngol Head Neck Surg,* 129:363-366; Rodrigo, et al., (2003) *Acta Otolaryngol* 123:100-105; Schliephake (2003) *Int J Oral Maxillofac Surg* 32:233-245). There is currently no effective molecular marker for HNSCC.

Given the foregoing, it would be desirable to have a marker to permit screening and early diagnosis of primary SCCs such as HSNCC, as well as for staging and prognosing the disease.

SUMMARY OF THE DISCLOSURE

Disclosed herein is the surprising discovery that chicken ovalbumin upstream promoter-transcription factor-interacting protein 2 (CTIP2; also known as Bcl11b, Rit1α, Rit1β, and Rit1γ) is a marker for squamous cell carcinoma, for example head and neck squamous cell carcinoma. In one embodiment, a method is disclosed for detecting squamous cell carcinoma (SCC) in a subject. The method can include detecting CTIP2 expression in a sample obtained from the subject, wherein an increase in expression of at least 2-fold relative to a reference value of CTIP2 expression for a sample negative for SCC indicates the presence of SCC in the sample obtained from the subject. In some embodiments, the SCC is HNSCC. In another embodiment, the SCC is a prostate, breast, lung, cervical, or ovarian SCC.

Also disclosed are kits for detecting SCC in a subject. The kit can include a CTIP2-specific antibody, a CTIP2-specific oligonucleotide, or a pair of CTIP2-specific primers, and a chart or diagram showing CTIP2 expression values that are expected in the presence of SCC (or a particular stage of SCC). Kits can also include control samples, such as a CTIP2 negative and/or positive sample (for example an SCC sample and a sample from the same tissue that does not have SCC). In some examples, the kit includes agents for detecting other molecules, such as BMI1. In one embodiment, the kit can detect the presence of breast SCC or HNSCC in a subject. In another embodiment, the kit can detect the presence of a prostate, lung, cervical or ovarian SCC.

Also provided are methods of screening for inhibitors of CTIP2. In some examples, the methods include contacting a test system that includes a CTIP2 polypeptide with at least one test agent, and then detecting in the presence of the at least one test agent: (a) decreased expression of a nucleic acid encoding the CTIP2 polypeptide; (b) decreased expression of the CTIP2 polypeptide; (c) a post-translational modification of the CTIP2 polypeptide; and/or (d) a decreased activity of the CTIP2 polypeptide; thereby identifying a test agent that can function as a CTIP2 inhibitor.

The foregoing and other features will become more apparent from the following detailed description of several embodiments, which proceeds with reference to the accompanying figures.

BRIEF DESCRIPTION OF THE FIGURES

FIG. 1A is a digital image showing that CTIP2 expression is restricted to the basal cell layers in normal epithelium. FIG. 1B is a digital image showing that expression in dysplastic epithelium is stronger than in normal epithelium, and this expression extends to the differentiated cell layers. FIG. 1C is a digital image showing that, in well differentiated tumors, positive staining is restricted to the basal layers at the periphery of the carcinomatous clusters. FIG. 1D is a digital image showing that homogeneous expression of CTIP2 was observed in tumor cells in moderately differentiated tumors. FIGS. 1E and 1F are digital images showing that CTIP2 expression of stronger intensity (score 3) was observed in poorly differentiated tumors. Arrows indicate the CTIP2-positive staining. Dotted lines represent the margin of epidermis and dermis (FIG. 1A), and margin of undifferentiated tumor cell clusters (FIGS. 1E and 1F).

FIG. 2 includes two panels showing immunohistochemical (IHC) staining intensities of CTIP2 in HNSCC. Staining intensities were graded as 0-3 as described in Example 1 of the Detailed Description.

FIG. 5A is a digital image showing that CTIP2 expression is restricted to the basal cell layers in normal epithelium. FIG. 5B is a digital image showing that expression in dysplastic epithelium is stronger than in normal epithelium, and this expression extends to the differentiated cell layers. FIGS. 5C and 5D are digital images showing that, in well differentiated tumors, positive staining is restricted to the basal layers at the periphery of the keratinized horn pearl. FIGS. 5E and 5F are digital images showing that homogeneous expression of CTIP2 was observed in tumor cells in moderately differentiated tumors. FIGS. 5G and 5H are digital images showing that CTIP2 expression of stronger intensity (score 3) was observed in poorly differentiated tumors. Arrows indicate the CTIP2-positive staining. Dotted lines represent the margin of epidermis and dermis (FIG. 5A), and margin of undifferentiated tumor cell clusters (FIG. 5E, which is magnified in 5F). The images in the insets of 5A, 5B, 5G and 5H are magnified (original magnification: 20×).

FIG. 6 shows staining intensities of CTIP2 by immunohistochemistry in HNSCC and other types of carcinoma.

FIG. 7A shows co-staining of CTIP2 and K10 in a dysplasia sample (upper panels) or moderately differentiated head and neck tumor (lower panels). Dotted lines represent the margin of epidermis and dermis. FIG. 7B shows co-staining of CTIP2 and Ki67 in a poorly differentiated head and neck tumor sample. Arrows refer to magnified insets shown below each corresponding image of FIG. 7B (original magnification 20×).

FIG. 9 is a graph showing relative quantification levels of CTIP2 in wild-type (WT) and knockout (KO) mice. Mean measurements (±S.E.M) are shown. A reduced level of expression of BMI1 was observed in the CTIP2 mutant mice. p values between the wild-type and CTIP2 mutant were significant (*p<0.05).

FIG. 10A is a graph showing the levels of human $CTIP2_L$ expression based on tumor size, tumor staging and differentiation status. The relative quantification levels are shown ±S.E.M. p values were not significant between the groups. FIG. 10B is a graph showing the levels of human CTIP2 expression based on tumor size, tumor staging and differentiation status. The relative quantification levels are shown ±S.E.M. p values were observed to be significant when associated with differentiation status.

SEQUENCE LISTING

Figure 1:
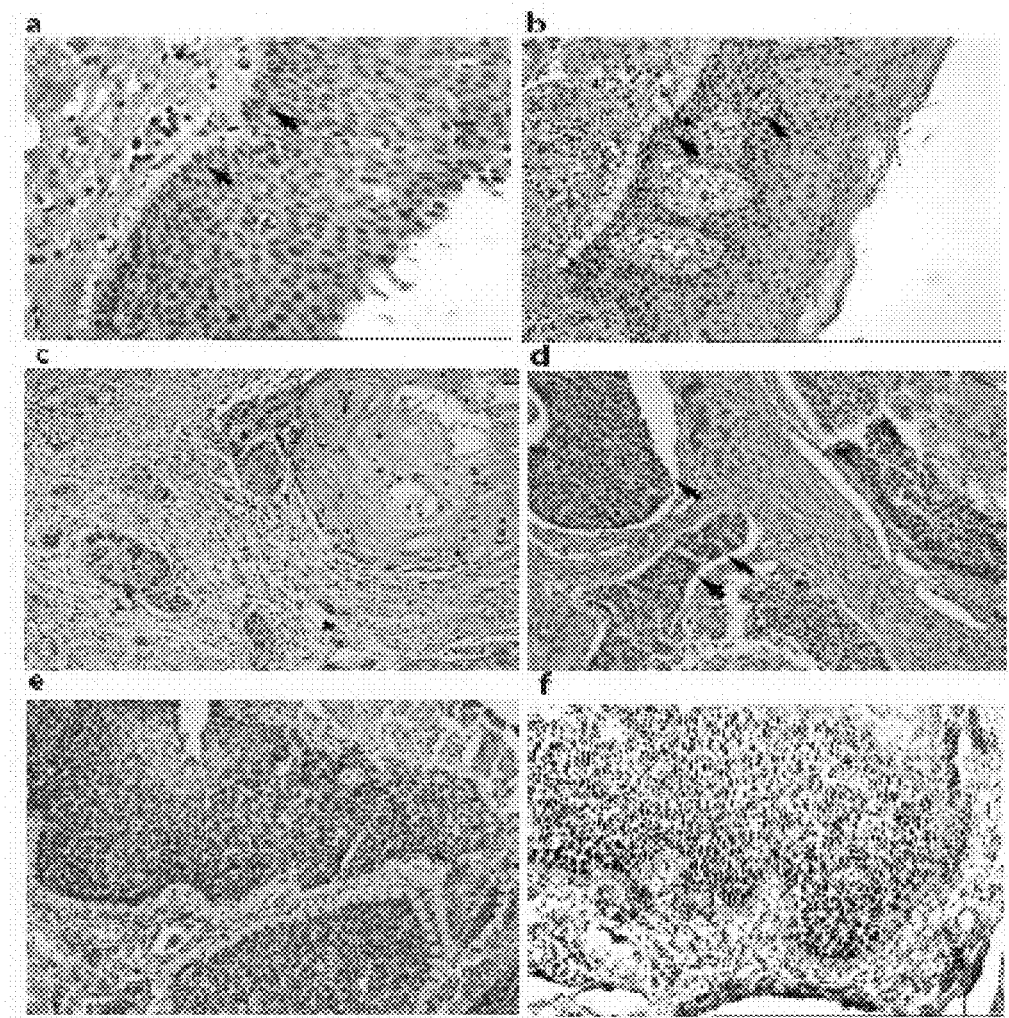
FIG. 1 includes several panels showing an immunohistochemical analysis of CTIP2 in HNSCC.

The nucleic acid sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand. In the accompanying sequence listing:

SEQ ID NO: 1 is a forward primer used to amplify $CTIP2_L$ (hCTIP2 E2-E3) ATCTGTCCCAAGCAGGAGAA SEQ ID NO: 2 is a reverse primer used to amplify $CTIP2_L$ (hCTIP2 E2-E3) GTCTGACCCTCACCCTGAGT SEQ ID NO: 3 is a forward primer used to amplify CTIP2 (hCTIP2 E2-E4) AGCAGGAGAACATTGCAGGTA SEQ ID NO: 4 is a reverse primer used to amplify CTIP2 (hCTIP2 E2-E4) GGAAATTCATGAGCGGGGACT

DETAILED DESCRIPTION

I. Overview of Several Embodiments

Disclosed herein are methods and kits for detecting, diagnosing, staging, and prognosing cancer, for instance squamous cell carcinoma. The methods and kits take advantage of the surprising discovery that chicken ovalbumin upstream promoter-transcription factor-interacting protein 2 (CTIP2) is a marker for squamous cell carcinoma, for example HNSCC. Squamous cell carcinoma cells, for example HNSCC cells, express CTIP2 at higher levels than do corresponding non-cancerous cells, and therefore CTIP2 expression levels can be used to detect SCC in a subject or sample, as well as to diagnose or stage the disease, to determine disease prognosis, or to determine whether a subject is responding (or will respond) to treatment for SCC.

One embodiment of the disclosure is a method for detecting squamous cell carcinoma in a subject, for example to diagnose SCC in a subject. In particular examples, the method includes detecting CTIP2 expression in a sample obtained from the subject, for example a biopsy, wherein an increase in CTIP2 expression of at least 2-fold relative to a reference value of CTIP2 expression for a sample negative for SCC (such as a normal head or neck sample) indicates the presence of SCC in the sample obtained from the subject. In certain embodiments, the SCC is HNSCC. In other embodiments, the SCC is a prostate, lung, breast, ovarian or cervical squamous cell carcinoma. In one embodiment, the method used to detect the at least 2-fold increase in CTIP2 expression of a sample obtained from a subject relative to a reference sample (negative for SCC) is a nucleic acid molecule expression method, such as PCR.

In some examples, detecting CTIP2 expression includes detecting CTIP2 protein expression, for example by contacting the sample with a CTIP2-specific antibody under conditions sufficient for binding of the antibody to CTIP2 proteins in the sample, thereby forming CTIP2-antibody complexes; and detecting the CTIP2-antibody complexes. In even more particular examples, detecting the CTIP2-antibody complexes includes contacting the CTIP2-antibody complexes with a secondary antibody that includes a label under conditions sufficient for binding of the secondary antibody to CTIP2-antibody complexes, thereby forming labeled-CTIP2-antibody complexes; and detecting the label. Any method used to detect proteins can be used to detect CTIP2, for example using routine immunohistochemistry methods (such as microscopy, ELISA, Western blotting, or flow cytometry) as well as mass spectrometry methods. In some embodiments, CTIP2 protein expression is quantified.

In other embodiments, detecting CTIP2 expression includes detecting CTIP2 nucleic acid molecule expression, for instance by detecting CTIP2 cDNA or mRNA expression. Any method used to detect nucleic acids can be used to detect CTIP2, such as PCR. In certain examples, detecting CTIP2 expression includes quantifying CTIP2 expression.

In some embodiments of the method, a second reference value of CTIP2 expression for a sample positive for squamous cell carcinoma is provided, wherein an amount of CTIP2 expression substantially similar to an amount of CTIP2 expression in the second reference value indicates the presence of squamous cell carcinoma in the sample obtained from the subject.

In other embodiments, the method also includes determining CTIP2 localization in cells present in the sample; and, comparing the CTIP2 localization to a reference CTIP2 localization sample, wherein CTIP2 localization substantially similar to the CTIP2 localization in the reference sample indicates that the subject has the presence, absence or grade of squamous cell carcinoma of the reference sample. In other examples, the method includes selecting subjects having at least a two-fold increase in CTIP2 expression (such as a 2-, 3-, 4-, 5- or 10-fold increase) for squamous cell carcinoma, for treatment of a squamous cell carcinoma. Still other examples of the method further include resecting head and neck squamous cell carcinoma cells from the subject, administering a therapeutic amount of a chemotherapeutic agent to the subject (such as a CTIP2 inhibitor), administering a therapeutic amount of a radio-therapeutic agent to the subject, or combinations thereof.

Particular embodiments further include quantitating CTIP2 expression. For instance, in certain examples, the level of CTIP2 expression is compared to a reference value of CTIP2 expression for a sample positive for poorly-differentiated squamous cell carcinoma, and an amount of CTIP2 expression that is substantially similar to an amount of CTIP2 expression in the reference value of CTIP2 expression indicates the presence of a poorly-differentiated squamous cell carcinoma in the sample obtained from the subject. In some examples, the presence of a poorly-differentiated squamous cell carcinoma in the sample obtained from the subject indicates a poor disease prognosis.

In some embodiments of the method, the increase in CTIP2 expression relative to the reference value is at least 3-fold, and in other embodiments, the increase in CTIP2 expression relative to the reference value is about 2-fold to about 10-fold. In particular examples, the increase in CTIP2 expression relative to the reference value is 2-fold. In certain embodiments, the method used to detect an increase in CTIP2 expression relative to a reference value is a nucleic acid molecule expression method, such as PCR.

In other embodiments of the method, the method can be used to determine if a subject will respond to CTIP2 inhibitor/antagonist therapy. In this example, an increase in CTIP2 expression relative to a reference value indicates that the subject will respond to CTIP2 inhibitor/antagonist therapy. A decrease (or no change) in CTIP2 expression relative to the reference value indicates that the subject is not likely to respond to CTIP2 inhibitor/antagonist therapy. In some embodiments, the increase in CTIP2 expression is at least about 10%, 20%, 30%, 40%, 50%, 60%, 70%, 80%, 90%, 95% or 99% increase in CTIP2 expression relative to the reference value. In certain embodiments, the method used to detect an increase in CTIP2 expression relative to a reference value includes an immunohistochemistry method.

Other embodiments are kits for detecting SCC in a subject. The kits include, for instance, a CTIP2-specific antibody, a CTIP2-specific oligonucleotide, or a pair of CTIP2-specific primers, and a chart or diagram showing CTIP2 expression values that are expected in the presence of SCC (or a particular stage of SCC). In a non-limiting example, the kit can be used to detect HNSCC in a subject. In another embodiment, the kit can be used to detect a breast, prostate, lung, ovarian, or cervical squamous cell carcinoma in a subject. The kits include, for instance, a CTIP2-specific antibody, a CTIP2-specific oligonucleotide, or a pair of CTIP2-specific primers, and a chart or diagram showing CTIP2 expression values that are expected in the presence of SCC. In certain examples, the oligonucleotide is capable of hybridizing under stringent conditions to CTIP2.

In other non-limiting embodiments, the kits can be used to determine differentiation status of a sample positive for SCC. In this example, the kit can include a $CTIP2_L$-specific antibody, a $CTIP2_L$-specific oligonucleotide, or a pair of CTIP2-specific primers specific for $CTIP2_L$ and a chart or diagram showing CTIP2$_L$ expression values that are expected in the presence of a particular stage of SCC.

In particular examples, the kit includes both a CTIP2$_L$-specific antibody, a CTIP2$_L$-specific oligonucleotide, or a pair of CTIP2$_L$-specific primers, and a CTIP2-specific antibody, a CTIP2-specific oligonucleotide, or a pair of CTIP2-specific primers. Some examples of the kit also include a buffer solution in separate packaging.

Other embodiments are methods of identifying a CTIP2 inhibitor, such as an agent that significantly reduces the biological activity of CTIP2. These methods can include contacting a test system comprising a CTIP2 polypeptide with at least one test agent; detecting in the presence of the at least one test agent (for example relative to the absence of the test agent): (a) decreased expression of a nucleic acid encoding the CTIP2 polypeptide; (b) decreased expression of the CTIP2 polypeptide; (c) a post-translational modification of the CTIP2 polypeptide; and/or (d) a decreased activity of the CTIP2 polypeptide; thereby identifying the test agent as a CTIP2 inhibitor. In some examples, the test system is tested in the absence of the test agent as a negative control. In some examples, the test system includes a subject having a head/neck cell that expresses the CTIP2 polypeptide, wherein contacting the test system includes administering the at least one test agent to the subject, and detecting includes detecting in the head/neck cell in the presence of the at least one test agent (a) decreased expression of a nucleic acid encoding the CTIP2 polypeptide; (b) decreased expression of the CTIP2 polypeptide; (c) a posttranslational modification of the CTIP2 polypeptide; and/or (d) a decreased activity of the CTIP2 polypeptide. In other examples, the test system includes a subject with a breast, lung, prostate, ovary or cervical SCC that expresses the CTIP2 polypeptide. In another example, the subject is a transgenic animal that overexpresses CTIP2 or is an NC/Nga mouse.

In still other examples, the method includes contacting an isolated cell that includes a CTIP2 polypeptide with the at least one test agent and detecting in the cell (a) decreased expression of a nucleic acid encoding the CTIP2 polypeptide; (b) decreased expression of the CTIP2 polypeptide; (c) a post-translational modification of the CTIP2 polypeptide; and/or (d) a decreased activity of the CTIP2 polypeptide. Optionally, in some examples, the isolated cell is an isolated head/neck cell or an isolated cell of a head/neck cell line, for instance, SCC-4, SCC-9, SCC-15, SCC-25, 92VU078, 93VU094, 93VU120, OHSU-974, VU1131-T2.8, or VU1365. In another example, the isolated cell is an isolated breast cell or an isolated cell of a breast cell line, for instance, MCF-7 or MCF10A.

In particular examples, the method of identifying CTIP2 inhibitors further includes selecting the agent and determining the isolated cell specificity of the: (a) decreased expression of a nucleic acid encoding the CTIP2 polypeptide; (b) decreased expression of the CTIP2 polypeptide; (c) post-translational modification of the CTIP2 polypeptide; and/or (d) decreased activity of the CTIP2 polypeptide; which is detected in the presence of the agent. Potential CTIP2 inhibitors identified using in vitro assays can be selected and further examined in an animal model.

II. Abbreviations bFGF: basic fibroblast growth factor
BMI1: polycomb ring finger oncogene
COUP-TF: chicken ovalbumin upstream promoter-transcription factor
CTIP2: chicken ovalbumin upstream promoter-transcription factor-interacting protein 2
CTIP2$_L$: chicken ovalbumin upstream promoter-transcription factor-interacting protein 2, long form
CTIP2$_S$: chicken ovalbumin upstream promoter-transcription factor-interacting protein 2, short form
DAPI: 4',6-diamidino-2-phenylindole
EGFR: epidermal growth factor receptor
FRET: Förster resonance energy transfer
G-CSF: granulocyte colony-stimulating factor
GM-CSF: granulocyte macrophage colony-stimulating factor
HIF: hypoxia-inducible factors
HNSCC: head and neck squamous cell carcinoma
HPV: human papillomavirus
K10: Cytokeratin 10
Ki-67: an antigen encoded by the MKI67 gene
MDM2: mouse double minute protein 2
MAGE: melanoma antigen
MMP: matrix metalloproteinase
NE: normal epithelium
OSC: oral squamous cancer
PCR: polymerase chain reaction
PDGF: platelet-derived growth factor
RT-PCR: reverse transcriptase-PCR
SSC: Squamous cell carcinoma
TIMPS: tissue inhibitors of metalloproteinases
TNM: tumor, node, metastasis
VEGF: vascular endothelial growth factor III. Terms Unless otherwise explained, all technical and scientific terms used herein have the same meaning as commonly understood by one of ordinary skill in the art to which the disclosed subject matter belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and/or Robert A. Meyers (ed.), *Molecular Biology and Biotechnology: A Comprehensive Desk Reference*, published by VCH Publishers, Inc., 1995 (ISBN 1-56081-569-8). In order to facilitate review of various embodiments of the disclosure, the following explanations of specific terms are provided:

Amplifying a nucleic acid molecule: To increase the number of copies of a nucleic acid molecule, such as a gene or fragment of a gene, for example a region of a CTIP2 gene. The resulting products are called amplification products.

An example of in vitro amplification is the polymerase chain reaction (PCR), in which a biological sample obtained from a subject (such as a head/neck cell sample) is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include quantitative real-time PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Quantitative real-time PCR is another method of in vitro amplification of nucleic acid molecules, enabled by Applied Biosystems (TaqMan PCR). The 5' nuclease assay provides a real-time method for detecting only specific amplification products. During amplification, annealing of the probe to its target sequence generates a substrate that is cleaved by the 5' nuclease activity of Taq DNA polymerase when the enzyme extends from an upstream primer into the region of the probe. This dependence on polymerization ensures that cleavage of the probe occurs only if the target sequence is being amplified. The use of fluorogenic probes makes it possible to eliminate post-PCR processing for the analysis of probe degradation. The probe is an oligonucleotide with both a reporter fluorescent dye and a quencher dye attached. While the probe is intact, the proximity of the quencher greatly reduces the fluorescence emitted by the reporter dye by Förster resonance energy transfer (FRET) through space. Probe design and synthesis has been simplified by the finding that adequate quenching is observed for probes with the reporter at the 5' end and the quencher at the 3' end.

Antibody: A molecule including an antigen binding site which specifically binds (immunoreacts with) an antigen. The term "antibody" includes immunoglobulin molecules and immunologically active portions thereof, as well as immunoglobulin-like molecules. Immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. In particular examples, a CTIP2-specific antibody is used to detect expression or localization of the CTIP2 in a cell. Antibodies include both monoclonal and polyclonal antibody preparations, as well as chimeric antibodies.

In some examples, an antibody specifically binds to a target (such as CTIP2) with a binding constant that is at least $10^3$ $M^{-1}$ greater, $10^4 M^{-1}$ greater or $10^5 M^{-1}$ greater than a binding constant for other molecules in a sample. In other examples, an antibody has a Kd value for binding to an antigenic determinant (such as a hapten or epitope) that is on the order of $10^{-6}$ M or lower, such as $10^{-9}$ M or lower, or even $10^{-12}$ M or lower. Kd values can, for example, be determined by competitive ELISA (enzyme-linked immunosorbent assay) or using a surface-plasmon resonance device such as the Biacore T100, which is available from Biacore, Inc., Piscataway, N.J.

Antibody fragments include proteolytic antibody fragments (such as F(ab')2 fragments, Fab' fragments, Fab'-SH fragments and Fab fragments), recombinant antibody fragments (such as sFv fragments, dsFv fragments, bispecific sFv fragments, bispecific dsFv fragments, diabodies, and triabodies), camelid antibodies (see, for example, U.S. Pat. Nos. 6,015,695; 6,005,079; 5,874,541; 5,840,526; 5,800,988; and 5,759,808), and antibodies produced by cartilaginous and bony fishes and isolated binding domains thereof (see, for example, International Patent Application No. WO03014161).

Array: An arrangement of molecules, such as biological macromolecules (such as CTIP2 peptides, antibodies, or nucleic acid molecules) or biological samples (such as breast, lung, prostate, ovary, cervix and head/neck tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least four, to at least 10, at least 20, at least 30, at least 50, at least 75, at least 100, at least 150, at least 200, at least 300, at least 500, least 550, at least 600, at least 800, at least 1000, at least 10,000, or more. In particular examples, an array includes nucleic acid molecules, such as oligonucleotide sequences that are at least 15 nucleotides in length, such as about 15-40 nucleotides in length.

In particular examples, an array includes oligonucleotide probes or primers which can be used to detect cancer-related sequences, such as at least four, at least 10, at least 20, at least 50, at least 100, at least 150, at least 175, at least 200, or at least 500 or more cancer-related sequences, for example SCC-related sequences, such as CTIP2 sequences. For example, an array may include one or more probes or primers specific for CTIP2, wherein the array is used to diagnose or prognose SCC. Such arrays can include "control" probes and primers, such as those that can detect housekeeping genes (for example beta-actin).

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including nucleic acids to which proteins are bound, or vice versa. In some examples, an array contains antibodies to cancer-associated proteins, such as any combination of at least four, at least 10, at least 20, at least 50, at least 100, at least 150, at least 175, at least 200, at least 500, or more cancer-related sequences, such as SCC-related sequences, for instance, CTIP2-related sequences. For example, an array may include one or more antibodies specific for CTIP2, wherein the array is used to diagnose or prognose SCC. Such arrays can include "control" antibodies, such as those that can detect housekeeping genes (for example beta-actin).

Chemotherapy: In cancer treatment, such as treatment of HNSCC, chemotherapy refers to the administration of one or more agents to kill or slow the reproduction of rapidly multiplying cells, such as tumor or cancer cells. In a particular example, chemotherapy refers to the administration of one or more anti-neoplastic agents to significantly reduce the number of tumor cells in the subject, such as a reduction of at least 10%, at least 20%, at least 30%, at least 40%, or at least 50%. Cytotoxic anti-neoplastic chemotherapeutic agents include, but are not limited to: 5-fluorouracil (5-FU), azathioprine, cyclophosphamide, antimetabolites (such as Fludarabine), and other antineoplastics such as Etoposide, Doxorubicin, methotrexate, Vincristine, carboplatin, cis-platinum and the taxanes (such as taxol). In a specific non-limiting example, cisplatin (such as Platinol®) and fluorouracil (such as Adrucil®, Efudex®) are used in combination and in addition to radiation to treat HNSCC.

CTIP2: Chicken ovalbumin upstream promoter transcription factor (COUP-TF)-interacting protein 2), is a C2H2 zinc finger protein that represses transcription through interaction with COUP-TF nuclear receptor proteins as well as through direct, sequence-specific DNA binding. It is expressed early during mouse development, as well as in the adult animal, and in both cases; expression is most predominant in the central nervous system, thymus, and skin/epithelial structures. It is shown herein that increased expression of CTIP2 is associated with SCC. As used herein, CTIP2 refers to the wild-type (native) form of CTIP2 that consists of exons 1, 2 and 4 (i.e., does not contain exon 3). As used herein, $CTIP2_L$ (CTIP2 long) refers to the full-length form of CTIP2 containing exons 1, 2, 3 and 4. $CTIP2_S$ (CTIP2 short), as used herein, refers to a shortened version of CTIP2 that consists of exons 1 and 4 and therefore lacks exons 2 and 3.

One specific, non-limiting example of a human CTIP2 protein sequence is GenBank Accession Number gi44887723 (herein incorporated by reference for the sequence available on Jun. 26, 2008). One specific, non-limiting example of a human CTIP2 nucleic acid sequence is GenBank Accession No. NM_022898 (herein incorporated by reference as of Jun. 26, 2008).

Detect: To determine if an agent is present or absent. In some examples, this can further include quantification. For example, antibodies specific for CTIP2 can be used to detect the presence of CTIP2 in a tissue or cell sample, for example by detecting a label associated with the CTIP2-specific antibody.

Diagnose: The process of identifying a medical condition or disease, for example from the results of one or more diagnostic procedures. In particular examples, diagnosing includes determining the prognosis of a subject. In one example, SCC is diagnosed by detecting CTIP2 expression in a tissue or sample, wherein significantly increased expression of CTIP2 (for example an at least 2-fold increase relative to a non-SCC sample) indicates the presence of SCC. In a specific example, HNSCC is diagnosed by detecting CTIP2 expression in an isolated tissue or cell sample, wherein significantly increased expression of CTIP2 (for example an at least 2-fold increase relative to a non-SCC sample) indicates the presence of HNSCC. For example, diagnosing can include determining the particular stage of SCC or HNSCC present.

Expression: The process by which the coded information of a gene is converted into an operational, non-operational, or structural part of a cell, such as the synthesis of a protein.

The expression of a nucleic acid molecule can be altered relative to a normal (wild type) nucleic acid molecule. Alterations in gene expression, such as differential expression, include but are not limited to: (1) overexpression; (2) underexpression; and (3) suppression of expression. Alterations in the expression of a nucleic acid molecule can be associated with, and in fact cause, a change in expression of the corresponding protein.

Protein expression also can be altered in some manner to be different from the expression of the protein in a normal (wild type or cancer-free) situation. This includes, but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard.

Controls or standards for comparison to a sample, for the determination of differential expression, include samples believed to be normal (in that they are not altered for the desired characteristic, for example a sample from a subject who has not had SCC), samples known to have disease or a marker of interest (e.g., CTIP2), samples from subjects with SCC, such as HNSCC as well as laboratory values, even though possibly arbitrarily set, keeping in mind that such values can vary from laboratory to laboratory.

Laboratory standards and values may be set based on a known or determined population value and can be supplied in the format of a graph or table that permits comparison of measured, experimentally determined values.

Head and neck squamous cell carcinoma (HNSCC): The term head and neck cancer refers to a group of biologically similar cancers originating from the upper aerodigestive tract, including the lip, oral cavity, nasal cavity, paranasal sinuses, pharynx, and larynx. Most head and neck cancers are squamous cell carcinomas, originating from the mucosal lining (epithelium) of these regions. Head and neck squamous cell carcinomas often spread to the lymph nodes of the neck, and this is often the first (and sometimes only) manifestation of the disease at the time of diagnosis. HNSCC is strongly associated with certain environmental and lifestyle risk factors, including tobacco smoking, alcohol consumption, and certain strains of the human papillomavirus (HPV). HNSCC can be treated if detected early, usually with some form of surgery, although chemotherapy and radiation therapy may also be needed.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide can be complementary to a CTIP2-encoding mRNA, or a CTIP2-encoding dsDNA.

"Specifically hybridizable" and "specifically complementary" are terms that indicate a sufficient degree of complementarity such that stable and specific binding occurs between the oligonucleotide (or it's analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization at 65° C. in 6×SSC, 5×Denhardt's solution, 0.5% SDS and 100 μg sheared salmon testes DNA, followed by 15-30 minute sequential washes at 65° C. in 2×SSC, 0.5% SDS, followed by 1×SSC, 0.5% SDS and finally 0.2×SSC, 0.5% SDS.

Increase: To make or be greater in the quality, amount, percentage or strength. For example, expression of CTIP2 in HNSCC is said to be "increased" relative to normal (e.g., non-cancerous) cells when the detected level of CTIP2 is at least 2-fold, such as at least 3-fold, at least 4-fold, or at least 10-fold greater in a test sample relative to a normal (e.g., non-cancerous) sample.

Isolated: An "isolated" biological component (such as a polynucleotide, polypeptide, or cell) has been purified away from other biological components in a mixed sample (such as a cell or tissue extract). For example, an "isolated" polypeptide or polynucleotide is a polypeptide or polynucleotide that has been separated from the other components of a cell in which the polypeptide or polynucleotide was present (such as an expression host cell for a recombinant polypeptide or polynucleotide).

The term "purified" refers to the removal of one or more extraneous components from a sample. For example, where recombinant polypeptides are expressed in host cells, the polypeptides are purified by, for example, the removal of host cell proteins thereby increasing the percent of recombinant polypeptides in the sample. Similarly, where a recombinant polynucleotide is present in host cells, the polynucleotide is purified by, for example, the removal of host cell polynucleotides thereby increasing the percent of recombinant polynucleotide in the sample. Isolated polypeptides or nucleic acid molecules, typically, comprise at least 50%, at least 60%, at least 70%, at least 80%, at least 90%, at least 95% or even over 99% (w/w or w/v) of a sample.

Polypeptides and nucleic acid molecules are isolated by methods commonly known in the art and as described herein. Purity of polypeptides or nucleic acid molecules may be determined by a number of well-known methods, such as polyacrylamide gel electrophoresis for polypeptides, or agarose gel electrophoresis for nucleic acid molecules.

Label: An agent capable of detection, for example by ELISA, spectrophotometry, flow cytometry, or microscopy. For example, a label can be attached to a protein or nucleic acid molecule, such as CTIP2, thereby permitting detection of the protein or nucleic acid molecule. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (*Molecular Cloning: A Laboratory Manual,* Cold Spring Harbor, N.Y., 1989) and Ausubel et al. (*In Current Protocols in Molecular Biology,* John Wiley & Sons, New York, 1998).

Neoplasm: An abnormal cellular proliferation, which includes benign and malignant tumors, as well as other proliferative disorders. In particular examples, a neoplasm is a squamous cell carcinoma such as a breast, lung, prostate or ovarian carcinoma. In one non-limiting example, a neoplasm is a head and neck neoplasm, for instance HNSCC.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide.

Particular oligonucleotides and oligonucleotide analogs can include linear sequences up to about 200 nucleotides in length, for example a sequence (such as DNA or RNA) that is at least 6 nucleotides, for example at least 8, at least 10, at least 15, at least 20, at least 21, at least 25, at least 30, at least 35, at least 40, at least 45, at least 50, at least 100 or even at least 200 nucleotides long, or from about 6 to about 50 nucleotides, for example about 10-25 nucleotides, such as 12, 15, or 20 nucleotides.

Oligonucleotide probe: A short sequence of nucleotides, such as at least 8, at least 10, at least 15, at least 20, at least 21, at least 25, or at least 30 nucleotides in length, used to detect the presence of a complementary sequence (e.g., a CTIP2 nucleic acid sequence) by molecular hybridization. In particular examples, oligonucleotide probes include a label that permit detection of the oligonucleotide probe:target sequence hybridization complex.

Primers: Short nucleic acid molecules, for instance DNA oligonucleotides 10-100 nucleotides in length, such as about 15, 20, 25, 30, or 50 nucleotides or more in length. Primers can be annealed to a complementary target DNA strand by nucleic acid hybridization to form a hybrid between the primer and the target DNA strand. Primer pairs can be used for amplification of a nucleic acid sequence, such as by PCR or other nucleic acid amplification methods known in the art.

Methods for preparing and using nucleic acid primers are described, for example, in Sambrook et al. (*In Molecular*

*Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length. Thus, for example, a primer including 30 consecutive nucleotides of a CTIP2-related nucleotide molecule will anneal to a target sequence, such as another homolog of the designated CTIP2-related protein, with a higher specificity than a corresponding primer of only 15 nucleotides. Thus, in order to obtain greater specificity, primers can be selected that include at least 20, at least 25, at least 30, at least 35, at least 40, at least 45, at least 50, or more consecutive nucleotides of a CTIP2-related nucleotide sequence.

Reference value: A number or range of numbers representing a particular condition. An experimental value can be compared to the reference value, for example to make a diagnosis or prognosis. For example, a reference value can be a relative or absolute amount (or range) of CTIP2 expression expected for a particular condition, such as normal (non-cancerous) cells, dysplasia (for example a particular stage of dysplasia), or SCC (for example a particular stage of cancer). In one example, a reference value can be a relative or absolute amount (or range) of CTIP2 expression expected for a particular condition, such as normal head and neck cells, dysplasia or HNSCC.

Sample: Biological specimens such as samples containing biomolecules, such as nucleic acid molecules, proteins, or both. Exemplary samples are those containing cells or cell lysates from a subject, such as those present in peripheral blood (or a fraction thereof such as serum), tissue biopsy, cheek swabs, surgical specimens, fine needle aspirates, head/neck cell or tissue samples, breast samples, lung or bronchi samples, prostate samples, ovarian, cervical or vaginal swabs or tissue samples, ulcerated tissue samples and autopsy material. In a specific example, a sample is obtained from the oral cavity, which can include cells from, for instance, the hard palate, the soft palate, the larynx, or the tongue.

Specific binding: Specific binding refers to the particular interaction between one binding partner (such as a binding agent, e.g., an antibody or probe) and another binding partner (such as a target, e.g., a CTIP2 protein or nucleic acid). Such interaction is mediated by one or, typically, more noncovalent bonds between the binding partners (or, often, between a specific region or portion of each binding partner). In contrast to non-specific binding sites, specific binding sites are saturable. Accordingly, one exemplary way to characterize specific binding is by a specific binding curve. A specific binding curve shows, for example, the amount of one binding partner (the first binding partner) bound to a fixed amount of the other binding partner as a function of the first binding partner concentration. As the first binding partner concentration increases under these conditions, the amount of the first binding partner bound will saturate. In another contrast to non-specific binding sites, specific binding partners involved in a direct association with each other (e.g., a protein-protein interaction) can be competitively removed (or displaced) from such association (e.g., protein complex) by excess amounts of either specific binding partner. Such competition assays (or displacement assays) are very well known in the art.

Squamous cell carcinoma (SCC): A form of cancer of the carcinoma type that can occur in many different organs, including the skin, lips, mouth, esophagus, urinary bladder, head and neck, prostate, lungs, vagina, ovaries and cervix. It is a malignant tumor of the squamous epithelium (epithelium that shows squamous cell differentiation). A carcinoma can be characterized as either in situ (confined to the original site) or invasive, depending on whether the cancer invades underlying tissues; only invasive cancers are able to spread to other organs and cause metastasis.

Squamous cell carcinoma is the second most common cancer of the skin (after basal cell carcinoma but more common than melanoma). The risk of metastasis is greater with SCC than with basal cell carcinoma.

Most cases of head and neck cancer (cancer of the mouth, nasal cavity, throat and associated structures) are due to squamous cell carcinoma. Treatment is usually with surgery (which may be extensive) and radiotherapy. Risk factors include smoking and alcohol consumption.

Esophageal cancer may be due to either SCC or adenocarcinoma (EAC). SCCs tend to occur closer to the mouth, while adenocarcinomas occur closer to the stomach.

SCCs also occur in the lung. When associated with the lung, ectopic production of parathyroid hormone-related protein is often observed, resulting in hypercalcemia.

When SCCs are associated with the prostate, the prognosis is generally poor because of the aggressive nature of this cancer. The initial lesions can be difficult to detect meaning that the cancer is often diagnosed at an advanced stage.

Vaginal squamous cell carcinoma spreads slowly and usually stays near the vagina, but may metastasize to the lungs and liver.

Primary squamous cell carcinoma of the ovary is relatively uncommon and has a poor prognosis due to its high mortality rate. This form of carcinoma is known to present with variable histological criteria, thus making an accurate and swift diagnosis assay for ovarian squamous cell carcinoma difficult to develop.

Breast squamous cell carcinoma is also rare and accounts for less than 0.075% of all primary invasive breast malignancies. Breast SCC is associated in the elderly.

Subject: Living multi-cellular vertebrate organisms, a category that includes human and non-human mammals (such as laboratory or veterinary subjects).

Under conditions sufficient for: A phrase that is used to describe any environment that permits the desired activity.

In one example, the term includes incubating a CTIP2 antibody with a tissue or cell sample under conditions that allow the antibody to specifically bind to CTIP2 proteins present in the sample.

The singular forms "a," "an," and "the" refer to one or more than one, unless the context clearly dictates otherwise. For example, the term "comprising a CTIP2-specific antibody" includes single or plural CTIP2 antibodies and is considered equivalent to the phrase "comprising at least one CTIP2 antibody." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Suitable methods and materials for the practice or testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification (see, for instance, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999). All sequences associated with the GenBank accession number related herein are incorporated by reference as of Jun. 26, 2008 (that is, the sequence present on Jun. 26, 2008, publicly available at the GenBank Website is incorporated by reference).

IV. CTIP2 is a Marker for Squamous Cell Carcinoma

Markers specific for squamous cell carcinomas (SCCs) are needed for early and effective detection of the disease. In other embodiments, markers are used to monitor the status of a carcinoma after surgery or therapy. The following provides a review of exemplary forms of SCC that can benefit from the compositions and methods disclosed herein. In one embodiment, one or more, for example, two or more of the following markers can be measured in conjunction with (or in addition to) CTIP2 or $CTIP2_L$ expression to detect the presence of SCC in a sample. In another embodiment, one or more, for example, two or more of the following markers can be used in conjunction with (or in addition to) CTIP2 or $CTIP2_L$ expression to determine the differentiation status of a SCC positive sample. In one embodiment, the markers measured in conjunction with, or in addition to CTIP2 expression may be up-regulated as compared to a normal (non-cancerous) reference sample. In another embodiment, the markers measured in conjunction with, or in addition to CTIP2 expression can be down-regulated in comparison to a non-cancerous reference sample. In some embodiments, the two or more markers measured in addition to CTIP2 expression may include an up-regulated marker and a down-regulated marker expression level as compared to a non-cancerous sample.

A. Breast Squamous Cell Carcinoma

Primary squamous cell carcinoma of the breast is rare with an unclear pathology and aggressive clinical behavior. Mitotic activity in this form of cancer may be high, and some samples have demonstrated high cellular proliferative index, as evaluated by staining with Ki67 antibody. Immunohistochemistry of breast SCC samples have been shown to be diffusely positive for high molecular weight cytokeratins such as cytokeratins 5 and 6, and C-erb-2 (the product of the HER-2 oncogene), while negative for vimentin, estrogen and progesterone (Megha et al., *Pathologica.*, 96(2):45-8, 2004). Additionally, a member of the p53 gene family, p63, has been expressed in breast samples with squamous cell differentiation (Koker et al., *Am. J. Surg. Pathol.*, 28(11): 1506-12, 2004). Other markers such as epidermal growth factor receptor (EGFR), HER-2, Cyclin B1 and hTERT have been investigated as potential markers of breast carcinoma. Typically, breast squamous cell carcinoma samples are observed to display a common profile exemplary of a basal origin: the samples do not express progesterone or estrogen receptors, are HER-2 negative, exhibit positively for cytokeratins 5/6, p63 and EGFR (Grenier et al., *Anticancer Res.*, 27(1B):547-55, 2007). The use of CTIP2 for the detection, diagnosis and treatment of breast SCC has not been previously proposed.

B. Cervical Squamous Cell Carcinoma

Cervical cancer is the most frequent disease of the reproductive organ and is the second most common cancer in women after breast cancer. As it is characterized by high mortality, new diagnostic methods are needed, for example to identify tumor markers that enable earlier diagnosis and rapid detection of recurrence after therapy. Although several different tumor markers have been identified that may be useful in the diagnosis of cervical carcinoma, for example squamous cell antigen (SCC-Ag), tissue polypeptide antigen (TPA), cytokeratin 19 (CYFRA), and mucins such as CA 15-3 and CA-125 (Davelaar et al., *Tumor Biol.*, 29(1):9-17, 2008), as well as some cytokines such as vascular endothelial growth factor (VEGF), granulocyte colony stimulating factor (G-CSF) and macrophage colony stimulating factor (M-CSF). Other molecular markers such as p53, Bcl-2, Brn-3a and MCM may also be useful as biomarkers of cervical cancer. The use of CTIP2 for the detection, diagnosis and treatment of cervical SCC has not been previously proposed.

C. Ovarian Squamous Cell Carcinoma

Mature Cystic Teratoma (MCT) of the ovary is the most common ovarian cystic disease in young women. Although it is a rare occurrence, some cases develop malignant transformation (MT)(about 2%). Preoperative diagnosis of squamous cell carcinomas arising in MCT of the ovary is a difficult task. Therefore, providing a marker to effectively diagnose a malignant transformation from MCT prior to surgery would be of significant clinical relevance. Mori et al. found that serum levels of SCC-Ag and patient's age were a reasonably successful marker for differential diagnosis between MCT and MT (*Gynecol. Oncol.* 90(2):338-41 (2003). In addition, combined use of serum macrophage colony stimulating factor (M-CSF) and SCC-Ag levels appeared to be useful in the selective diagnosis of MCT of the ovary harboring malignant SCC (Suzuki et al., *Gynecol. Oncol.*, 77(3):405-9, 2000).

However, use of CTIP2 has not been previously proposed to diagnose or prognose ovarian SCC.

D. Lung Squamous Cell Carcinoma

Carcinoembryonic antigen (CEA), squamous cell carcinoma antigen (SCC-Ag), neuron-specific enolase (NSE), cytokeratin 19 fragment (CYFRA), and pro-gastrin releasing peptide (proGRP) may be used as tumor markers for the diagnosis of lung cancer (Niho and Shinkai, *Gan To Kagaku Ryoho.*, 28(13):2089-93, 2001). In particular, SCC-Ag and CYFRA were observed to be sensitive for SCC, while NSE and proGRP showed enhanced sensitivity for small cell carcinoma. Kits for determining the serum level of CEA, SCC-Ag and CYFRA are commercially available and have been shown in some instances to be useful in the diagnosis of SCC (Tas et al., *J. Exp. Clin. Cancer Res.*, 19(4):477-81, 2000). However, CTIP2 has not been previously proposed as a marker of lung SCC.

E. Prostate Squamous Cell Carcinoma

Primary squamous cell carcinoma of the prostate is an uncommon malignancy, accounting for less than 1% of all prostate cancers, and is associated with a poor prognosis. The use of serum prostate-specific antigen (PSA) screening to facilitate early detection of prostate cancer has resulted in a dramatic increase in the number of prostate needle core biopsies which must be examined. This has been accompanied by a strong increase in the number of biopsies with ambiguous lesions. In particular, alpha-methyl-coenzyme-A-racemase (AMACR) has been proposed as a marker of prostate carcinoma that may be useful in confirming ambiguous lesions suspected of malignancy. CTIP2 has not been previously proposed as a marker of prostate SCC.

F. Head and Neck Squamous Cell Carcinoma

Head and Neck Squamous Cell Carcinoma (HNSCC) is an umbrella term that includes cancers at several sites (for example, the oral cavity, pharynx and larynx). HNSCC is the sixth most common form of cancer in the world. HNSCC accounts for over 90% of all head and neck cancers. Disappointingly, despite advances in surgical and other treatments that enhance quality of life and have palliative value, survival rates are not improving for this type of cancer. Treatment failures still occur in the form of local and regional recurrences, distant metastases, and/or second primary tumors.

SCCs are common in the oral cavity, including the inner lip, tongue, floor of mouth, gingivae, and hard palate. Cancers of this region, particularly the tongue, are more frequently treated with surgery than are other head and neck cancers. Surgeries for oral cancers include maxillectomy, mandibulectomy, glossectomy, radical neck dissection, Moh's procedure, and combinational surgeries, e.g. glossectomy and laryngectomy performed together.

HNSCC also originates in the nasopharynx, the oropharynx (often strongly associated with human papillomavirus infection), the hypopharynx, the larynx, and the trachea. Tumors of the hypopharynx frequently have an advanced stage at diagnosis, and have the most adverse prognoses of pharyngeal tumors. They tend to metastasize early due to the extensive lymphatic network around the larynx. Laryngeal cancer is strongly associated with tobacco smoking.

After a histologic diagnosis has been established and tumor extent determined, the selection of appropriate treatment for a specific cancer depends on a complex array of variables, including tumor site, relative morbidity of various treatment options, patient performance and nutritional status, concomitant health problems, social and logistic factors, previous primary tumors, and patient preference. Surgical resection and radiation therapy are the mainstays of treatment for most head and neck cancers and remain the standard of care in most cases. For small primary cancers without regional metastases (stage I or II), wide surgical excision alone or curative radiation therapy alone is used. More extensive primary tumors, or those with regional metastases (stage III or IV), planned combinations of pre- or postoperative radiation and complete surgical excision are generally used.

After surgery, radiation therapy is the most common form of treatment, such as intensity-modulated radiotherapy (IMRT). However, if the cancer has metastasized or is widespread, the older form of treatment may be the most effective at slowing the progression of the disease.

Chemotherapy in throat cancer is not generally used as a curative approach. Instead, it is used to provide an inhospitable environment for metastases so that they will not establish in other parts of the body. Typical chemotherapy agents are a combination of Taxol and Carboplatin. Erbitux is also used in the treatment of HNSCC. While not specifically a chemotherapy, Amifostine is often administered intravenously by chemotherapy clinic prior to a patient's radiotherapy sessions. Amifostine protects the patient's gums and salivary glands from the effects of radiation. Other forms of therapy include cetuximab, bevacizumab, and erlotinib.

Currently, treatment strategies rely on clinical, radiologic, and histopathologic parameters to determine the stage of the disease. It is widely accepted that the presence of lymph node metastases is the most adverse independent prognostic factor in HNSCC. Furthermore, tumors might differ according to their primary site, because the behavior of oral cancer is quite different from those of a laryngeal origin, for example. Wide heterogeneity in terms of clinical outcome and response to treatment exists even in patients who are assigned to the same risk group. Therefore, the current etiological focus in HNSCC is on the identification of better biological and clinical factors which may serve as prognostic and predictive markers. Although a variety of molecular tumor markers in have been identified, none of the markers has proven to be effective for predicting disease outcome or response to therapy. Until now, the use of CTIP2 as a diagnostic and prognostic marker for HNSCC has not been proposed.

G. Markers for HNSCC

A number of potential molecular markers have been evaluated in HNSCC prior to this disclosure. These are summarized as markers for: 1) tumor growth, proliferation and apoptosis, 2) tumor suppression, 3) tumor angiogenesis, 4) tumor invasion and metastasis, and 5) other markers. The following provides a review of HNSCCs that can benefit from the compositions and methods disclosed herein. In one embodiment, one or more, for example, two or more of the following HNSCC markers can be measured in conjunction with (or in addition to) CTIP2 or $CTIP2_L$ expression to detect the presence of HNSCC in a sample. In another embodiment, one or more, for example, two or more of the following HNSCC markers can be used in conjunction with (or in addition to) CTIP2 or $CTIP2_L$ expression to determine the differentiation status of a HNSCC positive sample.

1. Tumor growth, proliferation and Apoptosis

Epidermal Growth Factor Receptor

Epidermal Growth Factor Receptor Family (EFGR, Her-2/neu, c-erbB 3-4) is an extensively studied receptor tyrosine kinase that plays a vital role in cell growth, migration, metabolism, differentiation, and survival. The EGFR family includes EGFR, HER-2/neu (c-erbB-2), HER-3 (c-erbB-3), and HER-4 (c-erbB-4). Comprehensive data over the past 20 years strongly support the role of EGFR and its ligands in the development and progression of HNSCC. EGFR is overexpressed in a number of human solid tumors including HNSCC, leading to a survival impact based on EGFR expression levels in patients with advanced head and neck cancer. Overexpression of EGFR is observed in 42% to 80% of studied HNSCCs. Multivariate analysis of seven of the eight trials revealed a poorer outcome for patients with EGFR overexpression.

HER-2/neu

The HER-2/neu proto-oncogene is amplified and overexpressed in approximately 30% of human breast cancers and in several other tumors, including ovarian, gastric, and colorectal cancers, and the prognostic relevance of HER-2/neu has been documented in these tumors. Most data on the role of the HER-2/neu oncogene in HNSCC have been based on detection of the p185 protein by immunohistochemical techniques, and overexpression of HER-2/neu ranging from 0% to 47% has been reported. However, the prognostic significance of this oncogene is doubtful in HNSCC tumors.

Cyclin D1

Cyclins are a diverse family of proteins (A, B, D, and E), and are important during the cell cycle. Cyclin D1 (also known as PRAD1) is a proto-oncogene that responds to extracellular mitogens and is a controller of G1 phase progression through the cell cycle. The Cyclin D1 gene is amplified, rearranged, and overexpressed frequently in human cancer, including squamous cell carcinoma. The most commonly reported alteration of cyclin D1 is gene amplification (11q13). This results in the expression of a structurally normal protein, but at abnormally high levels, which leads the cell to a state of uncontrolled proliferation. Cyclin D1 is amplified in 30% to 50% of laryngeal carcinomas, and its deregulation increases the aggressiveness of certain cancers. Cyclin D1 expression is significantly correlated with tumor extension and advanced clinical stage (p=0.002 and p=0.001, respectively). The prognostic significance of Cyclin D1 is still not clear, although there may be a relationship between Cyclin D1 overexpression/amplification and poor outcome.

Ki67

Ki67, is a large molecular weight protein that is only expressed during the G1 to M phases of the cell cycle, and was thought to be a potential prognostic biomarker of HNSCC. The expression of Ki67 is significantly increased both in less-differentiated tumors and in those with lymph node metastases, compared with those without metastases. A correlation exists between the percentage of Ki-67-labelled cells at the time of the surgery and the TNM (Tumor, Node, Metastasis) stage. Ki-67 expression is highly correlated with histological grading, and is associated with neck metastases, but inversely correlated with the degree of cancer cell differentiation in human oral squamous cell carcinoma. Due to conflicting data, Ki67 is not an effective prognostic biomarker for HNSCC.

BMI1

BMI1 polycomb ring finger oncogene, also known as BMI1, is a protein that in humans is encoded by the BMI1 gene. Several groups have postulated that BMI1 is important for the self renewal of hematopoietic, neuronal stem cells as well as cancer stem/progenitor cells. To date, there has been no association of BMI1 expression and CTIP2 expression with the development of squamous cell carcinoma.

Bcl2

The bcl-2 family of proteins influences apoptosis, and some family members, like Bax, promote apoptosis, while others, like bcl-2, inhibit apoptosis. Bcl-2 overexpression has been associated with poor prognosis in some types of cancer (breast, colon and lung), favorable prognosis in others (cervix, melanoma, bladder and prostate), and no basis for designation in yet others (head and neck, endometrium, gastric etc.). No association was also found between Bcl-2 overexpression and outcome of the patient in two out of six studies.

Fas/FasL

The Fas receptor protein is normally expressed on most epithelial cells. It triggers apoptosis when in contact with the Fas-ligand, mainly through activation of caspase 3, a downstream protein of the apoptotic signal transduction cascade. Functional FasL has been reported to be up-regulated in many tumors such as esophagus, lung, and colon. Fas expression was observed in 100% of all the samples of tongue squamous cell carcinoma tested. No Fas receptors were detected in poorly differentiated tumors, which might indicate a lack of activation of apoptotic pathway. However, the role of Fas in prognosis in patients with HNSCC has not been defined.

2. Tumor Suppression p27 p27 (Kip1) is a cyclin-dependent kinase inhibitor, a member of the Cip/Kip group, which negatively regulates the G1 phase progression of the cell cycle by binding to the cyclinE/cyclin-dependent kinase-2 complex. p27 is activated in response to extracellular signals such as serum deprivation, contact inhibition, TGF-β, cyclic-AMP, and a growth inhibitory drug (rapamycin). p27 is not a frequent target of mutations predisposed to cancer, and is considered a tumor suppressor gene. Overexpression of p27 was observed in HNSCC cell lines. Reduced expression was associated with poor prognosis in precancerous lesion. Other studies showed that patients with metastases had lower levels of p27 compared with patients with tumors and no metastases. In another study, no difference in survival was observed in 93 patients with laryngeal and oral cavity carcinoma. Although, p27 plays a very important role in the cell cycle and carcinogenesis, it is not yet an acceptable marker for clinical decision making in HNSCC.

p53 p53 was discovered in the late 1970s as a critical modulator of the cellular response to exogenous and endogenous stress. Inactivation of one or more components of the p53 network is an extremely common event in human neoplasia. However, other mechanisms of inactivation, such as the presence of human papillomavirus (HPV) and molecular abnormalities in other components of this pathway have also been reported. In patients with HNSCC who have HPV, this may occur by means of the interaction of p53 with the E6 protein encoded by so-called oncogenic HPV types, mainly HPV16 and HPV18. Another mechanism involves mouse double minute protein 2 (MDM2), which binds to p53 and promotes the ubiquitination of the C-terminus of p53 and its subsequent degradation. Expression levels of MDM2 combined with p53 assessed by immunohistochemistry have been associated with tumor proliferation oral squamous cell carcinoma. In addition, combined expression levels of p53/p21 and p53/mdm2/p21 have been reported as significantly correlated with lymph node metastases. Similarly, p53 expression was positively associated with nodal involvement in 53 patients with laryngeal and tongue SCC. Conversely, p53 was not an independent predictor of metastases in 70 patients with advanced HNSCC.

In patients with HNSCC, multivariate analysis showed no prognostic value in 5 of 17 studies using immunohistochemistry to detect a p53 mutation. A significantly worse overall survival was found in patients with p53 overexpression in nine trials. Other studies identified either a worse disease-free survival, or local recurrence in patients overexpressing p53 than in those not overexpressing p53. In laryngeal carcinoma, worse overall survival was found in 62 patients, and worse DFS was reported in 83 patients.

In patients with HNSCC treated with cisplatin and 5-fluorouracil in a neoadjuvant setting, those whose disease was unresponsive to treatment had a higher prevalence of p53 mutations than responders. Similarly, p53 expression was a strong predictor of poor response in 236 patients with HNSCC treated with induction chemotherapy containing cisplatin and 5-fluorouracil. p53R2 mRNA expression, a new p53 target, has been used as a marker to predict tumor development and sensitivity to radio chemotherapy in oral squamous cell carcinoma. The discovery of p53 auto-antibodies has created a new serologic method to detect these cells in HNSCC. p53 and p27 are the two most studied molecular markers involved in tumor suppression in HNSCC.

3. Tumor Angiogenesis
VEGF

Angiogenesis is the growth of new microvessels, and this process depends on the motility, proliferation, and tube formation of endothelial cells. The vascular endothelial growth factor (VEGF) family contains specific and highly potent angiogenic proteins that act to increase vessel permeability, endothelial cell growth, proliferation, migration, and differentiation. At least six members of the VEGF family have been identified so far, including VEGF-A/vascular permeability factor, placenta growth factor, VEGF-B/VEGF-related factor, VGFR-C/VEGF-related protein, VEGF-D/c-fos-induced growth factor, and VEGF-E. VEGF and basic fibroblast growth factor (bFGF) are mitogenic and chemotactic for endothelial cells and are known to accumulate at the site of angiogenesis in situ. A study of 31 patients with oral squamous cell carcinoma reported the circulating level of VEGF and its relationship with clinico-pathologic features and prognosis. Elevated pretreatment serum VEGF levels tended to indicate an aggressive disease state and a short overall survival. VEGFR3 and its ligand VEGF-C was detected by semi-quantitative reverse transcriptase-PCR (RT-PCR) in four HNSCC cell lines and six HNSCC specimens and by IHC in another 18 HNSCC tumor specimens from 18 patients. No correlation was found between the expression of VEGF-C and clinical parameters.

The expression of several angiogenic cytokines was evaluated in vivo, including VEGF, bFGF, platelet-derived growth factor (PDGF)-AB, PDGF-BB, granulocyte colony-stimulating factor (G-CSF), and granulocyte macrophage colony-stimulating factor (GM-CSF) in HNSCC. Tumors producing at least three cytokines revealed a significantly poorer patient prognosis, with a worse overall survival in univariate analysis, than tumors that did not produce these cytokines.

Hypoxia-inducible factors (HIF1 and HIF2) are key proteins for response to hypoxic stimulus. The normal head and neck mucosa does not show any immunoreactivity for these two factors. In HNSCC, overexpression of HIF1 and HIF2 is significantly associated with high micro-vessel density, VEGF expression, incomplete response to chemotherapy, and a poor local relapse-free survival and overall survival.

4. Tumor Invasion and Metastatic Potential

Matrix metalloproteinases (MMPs) are a family of zinc metalloenzymes that are involved in extracellular matrix remodeling. Malignant cells use MMPs to help break down the basement membrane and degrade interstitial stroma, thus facilitating tumor invasion and/or metastasis. The expression of MMPs in oral squamous cancer (OSC) correlates with tumor stage. However, several published reports showed controversial results of MMPs and their tissue endogenous inhibitors (tissue inhibitors of metalloproteinases; TIMPs) in relation to tumor progression, as well as to the association between the plasma activity of these enzymes and the known clinical and pathologic parameters of patients with head and neck carcinoma.

5. Other Markers:
MAGE

The melanoma antigen (MAGE) genes encode certain tumor-associated antigens recognized by cytotoxic T lymphocytes. The presence or absence of three antigens identified to stimulate immune response, namely, NY-ESO-1, MAGE-1, and MAGE-3, in 45 HNSCC specimens were studied by either RT-PCR or immunohistochemistry. No correlation was found between antigen expression and patient demographics.

Galectin-3

Galectin-3, an endogenous lectin that reacts with glycan epitopes of membrane and extracellular glycoproteins, were assessed in primary HNSCC (from the tonsil, base of the tongue, and larynx), and lymph node metastases. Galectin-3 was found to be bound to a non-proliferating pool of tumor cells and localized with desmosomal proteins, suggesting that galactin-3 might be a potential new tool for monitoring the degree of cell differentiation in HNSCC. Unfortunately, these markers are still not ready, and a better understanding of their role as prognostic markers in HNSCC is necessary.

Micro-Array Analyses

Large-scale differential display comparison of hypopharyngeal SCC and histologically normal tissue identified 70 genes that exhibit a striking difference in expression in tumor versus normal tissue. In another study, patients with hypopharyngeal SCC had six overexpressed genes (EIF4G1, DVL3, EPHB4, MCM7, BRMS1, and SART1) and, from the comparison of patients with nonaggressive and aggressive tumors (without or with clinical evidence of metastases 3 years after surgery), 164 different expressed genes were involved in the acquisition of metastatic potential.

Smad2 protein was expressed in 99% of 170 HNSCC specimens. The activated form of Smad2, pSmad2, was expressed in 86% of these tumors, indicating their ability to survive and proliferate despite the presence of bioactive TGF-β within the tissue microenvironment. Using Atlas human cancer 1.2 cDNA array in 1187 tumor-related genes in either radio-resistant or radiosensitive tumors, 60 tumor-related genes were selected as a predictors of radiation response of HNSCC.

However, none of these markers are effective as prognostic and predictive factors. Thus, there remains a need for new biomarkers for HNSCC for use as diagnostic, prognostic, and predictive tools.

H. CTIP2 as a Marker for SCC

Chicken ovalbumin upstream promoter-transcription factor (COUP-TF)-interacting protein 2 (CTIP2, Bcl11b) is a transcriptional repressor (zinc finger protein) that functions by direct, sequence-specific DNA binding activity or by recruitment to the promoter template by interaction with COUP-TF family member (Avram, et al., (2000) *J Biol Chem*, 275:10315-10322; Avram, et al., (2002) *Biochem J*, 368:555-563; Topark-Ngarm, et al., (2006) *J Biol Chem* 281:32272-32283).

CTIP2 is expressed early during mouse development as well as in the adult animal, and in both cases; expression is most predominant in the skin/epithelial structures, CNS and thymus (Golonzhka, et al., (2007) *Gene Expr Patterns* 7:754-760; Leid, et al., (2004) *Gene Expr Patterns* 4:733-739).

Figure 8:
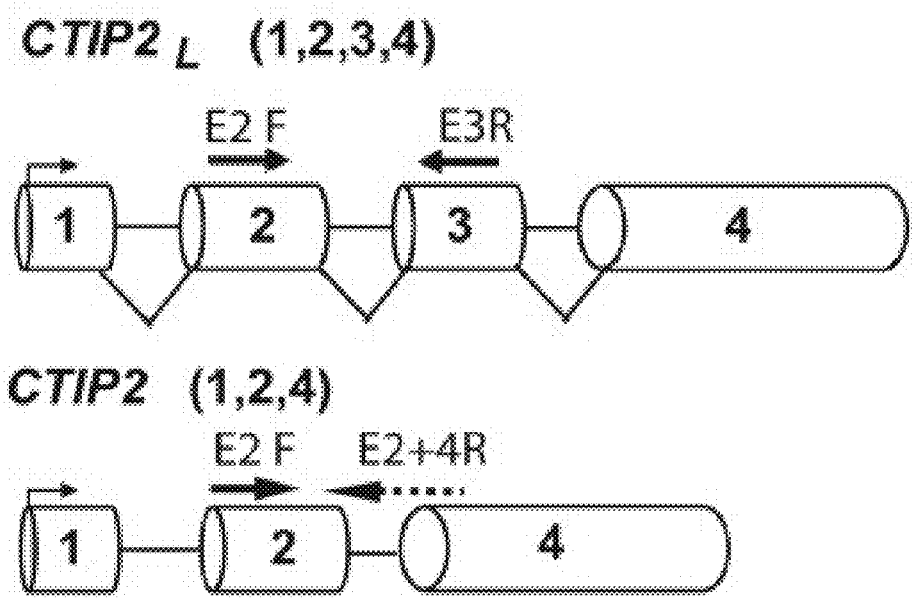
FIG. 8 shows a schematic of two CTIP2 transcripts, $CTIP2_L$ and CTIP2.

Human CTIP2 has three alternatively spliced transcript variants, which encode distinct isoforms (see FIG. 8). In the present disclosure, the variant lacking both exon 2 and exon 3 is termed $CTIP2_S$ (CTIP2 short). The variant containing all 4 exons is referred to as $CTIP2_L$ (CTIP2 long); and the variant lacking exon 3, which is the native form, is referred to as CTIP2 (or WT).

As described herein, CTIP2 expression is a biomarker in human SCC. Example 2, below, describes the examination of CTIP2 expression patterns using immunohistochemistry (IHC) and QRT-PCR, and the finding of a correlation between clinicopathological factors and CTIP2 expression in a panel of HNSCC samples. CTIP2 expression was analyzed on 40 paraffin-embedded archival specimens and 28 cDNA samples of HNSCC by IHC and QRT-PCR. Using IHC, a weaker staining of CTIP2 was observed in basal layer of head and neck tissue adjacent normal tissue. In well-differentiated tumors, CTIP2 staining was restricted to the basal layers at the periphery of the carcinamatous clusters, and the staining was weaker. Stronger and homogeneous expression of CTIP2 was observed in moderately/poorly differentiated tumors. The expression of CTIP2 in HNSCC samples was significantly higher (p<0.0175) compared to adjacent normal tissue. As determined by IHC, the CTIP2 staining pattern and percent positively in moderately and poorly differentiated tumors (over normal samples) was about a 50% increase. For example, Example 2, below, describes an increase of about 50% to about 75% CTIP2 expression in moderately and poorly differentiated tumors over normal samples. The higher expression levels CTIP2 protein significantly correlated with the poor histological tumor differentiation (P<0.02). Immunohistochemical analysis confirmed 16/40 samples with level 3 (0-1 staining intensities), 7/40 level 2, 12/40 level 1, and 5 with no staining at all. Thus, in one embodiment, methods of tumor staging are described comprising, normalizing relative quantification of CTIP2 staining to staining of a reference gene, such as ribosomal phosphor-protein PO(RPLPO), comparing the staining values between the two genes by statistical analysis, such as t-test or 1 way ANOVA, and correlating the extent of normalized CTIP2 staining against tumor staging, wherein an increased level of CTIP2 staining as compared to the reference gene is indicative of a poorly differentiated SCC.

The expression of the CTIP2 (native CTIP2) and a longer transcript ($CTIP2_L$) was examined using QRT-PCR, with primer sets that distinguished between the native form (CTIP2) and the longer variant ($CTIP2_L$). The correlation between CTIP2 expression and the clinicopathological parameters were assessed. No statistical significant correlation was found between CTIP2 expression and clinicopathological parameters (T stage, clinical stage and differentiation status) for $CTIP2_L$, however a higher expression of CTIP2 was significantly related to the poor differentiation state of the tumor (P<0.05), and a correlation was observed between expression and advanced T or clinical stage for CTIP2. Thus, CTIP2 expression is linked to a poor differentiation status, a higher chance of metastasis, and a lower survival rate (e.g. less than 5 years, less than 3 years, less than 1 year, or less than 6 months).

I. Methods of Detecting Dysplasia and SCC

The present disclosure provides methods that can be used to detect squamous cell carcinoma, for example prostate, lung, head and neck, breast, cervical and ovarian squamous cell carcinoma. Detection can include determining whether a tumor or condition is a SCC, for example a HSNCC, by grading the HNSCC (for example determining if it is a Stage 0, Stage I (such as Stage IA, IA1, IA2, IB1, IB2), Stage II (such as IIA or IIB), Stage III (such as IIIA or IIIB), or Stage IV (such as IVA or IVB) HNSCC), determining the prognosis of a subject found to have a HNSCC, or combinations thereof.

In particular examples, the method includes detecting CTIP2 expression in a tissue or cell sample obtained from the subject, such as detecting CTIP2 protein expression or nucleic acid molecule expression. In particular examples, the expression levels are quantitated. Methods of detecting protein or nucleic acid molecule expression are well known in the art.

In particular examples, the presence of a significant increase in expression of CTIP2, such as at least a 2-fold increase, relative to a level of CTIP2 expression in a corresponding normal tissue (non-cancerous and non-dysplastic), indicates the presence of SCC in the cell or tissue sample obtained from the subject. For example, the presence of at least a 2-fold increase in expression of CTIP2 in the test head or neck sample relative to a level of CTIP2 expression in a normal head or neck sample (non-cancerous and non-dysplastic), indicates the presence of HNSCC in the test sample obtained from the subject. In specific examples, detection of an at least 2-fold increase (such as at least 3-fold, at least 4-fold, or about 2- to about 10-fold) in expression of the CTIP2, relative to such expression in normal tissue, indicates the presence of a SCC in the cell or tissue sample obtained from the subject.

The detected CTIP2 expression can be compared to a reference value or reference sample representing a particular disease or disease-free state (such as normal tissue or a SCC sample, or a particular stage of SCC). For example, the detected level of CTIP2 expression in the sample can be compared to a level of CTIP2 expression in one or more reference tissue samples or to a reference value representing expected CTIP2 expression in a control tissue sample. Exemplary reference samples and values include those representing a known presence, absence, or grade of dysplasia or prostate, lung, breast, cervical, ovarian or head and neck SCC. For example, if the detected level of CTIP2 expression in one tissue is substantially similar to the level of CTIP2 expression in a particular reference sample or value for the same tissue, this indicates that the subject has that presence, absence or grade of dysplasia or SCC represented by the reference sample or value. In a specific example, if the reference value or sample is normal (non-dysplastic, non-cancerous) head and neck cells, a detected increase in CTIP2 expression of at least 2-fold (such as at least 3-fold) relative to such a reference value indicates the presence of HNSCC in the sample obtained from the subject.

In a specific example, detection of ovarian SCC is performed. If the detected level of CTIP2 in the test sample is substantially similar to the level of CTIP2 expression in a particular ovarian reference sample or value, this indicates that the subject has that presence, absence or grade of ovarian SCC represented by the reference sample or value. For example, if the detected relative value of CTIP2 expression is 50, and the reference value for CTIP2 expression is 10 for normal ovarian tissue, the reference value for CTIP2 expression is 40 for ovarian cell dysplasia, and the reference value for CTIP2 expression is 100 for ovarian SCC, then it is concluded that the subject has ovarian cell dysplasia. Similar methods can be used to determine whether the subject has normal, dysplasic, or cancerous ovarian cells using CTIP2 and the appropriate reference values or samples. Similar methods can be used for other SCCs.

In a specific example, the reference value or sample is normal head and neck cells (non-dysplastic, non-cancerous), and expression of CTIP2 is detected, wherein an at least 2-fold (such as at least 3-fold to about 10-fold) increase in CTIP2 expression relative to the reference value indicates the presence of head and neck cell dysplasia or HNSCC in the sample obtained from the subject.

The disclosed methods can include detecting variant forms of CTIP2 in a tissue sample such as CTIP2 and $CTIP2_L$. For example, the method can include determining the expression level of CTIP2, wherein an at least 2-fold increase relative to a reference value for expression of CTIP2 in normal tissue (non-cancerous and non-dysplastic), indicates the presence of SCC with a poorly-differentiated state in the sample obtained from the subject, which corresponds to a poor prognosis. In specific examples, detection of an at least two-fold, at least four-fold, at least five-fold, at least seven-fold, or at least a ten-fold increase in CTIP2 expression, relative to such expression such as in normal head and neck tissue, indicates the presence of HNSCC in the head and neck tissue sample obtained from the subject. In another specific example, detection of an at least two-fold, at least four-fold, at least five-fold, at least seven-fold, or at least ten-fold increase in CTIP2 expression in a prostate sample, relative to such expression in normal prostate tissue, indicates the presence of SCC with a poorly-differentiated state in the prostate tissue sample obtained from the subject. In one embodiment, the tissue sample from the subject utilized to detect an at least two-fold increase in CTIP2 expression relative to such expression in a corresponding normal (non-cancerous) tissue sample may be a lung, breast, cervical or ovarian tissue sample.

The method of detecting dysplasia or SCC can also include determining the localization pattern of CTIP2 in a tissue sample. In one example, the method of detecting dysplasia or SCC can include determining the localization pattern of CTIP2 in a tissue sample. The location of CTIP2 in a tissue sample can be compared to one or more reference values or samples having a known presence, absence or grade of dysplasia or SCC. For example, if the detected CTIP2 localization is substantially similar to the CTIP2 localization in a particular reference sample or value, this indicates that the subject has that presence, absence or grade of dysplasia or SCC represented by the reference sample or value. In a specific example, if the reference value or sample is normal (non-dysplastic, non-cancerous), such as normal head and neck cells, and a detected CTIP2 localization is observed in a sample obtained from a subject (such as increased localization in the differentiated layers) relative to the reference value, this indicates the presence of dysplasia in the sample obtained from the subject. Similarly, increased CTIP2 expression in the basal layers at the periphery of a tumor indicates the presence of a well-differentiated SCC tumor, whereas more homogeneous CTIP2 expression is indicative of a moderately- or poorly-differentiated SCC tumor.

J. Detecting CTIP2 Protein Expression

Methods of detecting a protein in a sample are well known in the art. For example, immunoassays and immunocytology methods can be used, as well as mass spectrometry methods. For example, any standard immunoassay format (such as ELISA, Western blot, or RIA assay) can be used to measure and/or quantify CTIP2 protein levels. In some examples, CTIP2 proteins are detected and quantitated, for example using antibody probe arrays, quantitative spectroscopic methods (for example mass spectrometry, such as surface-enhanced laser desorption/ionization (SELDI)-based mass spectrometry), or combinations thereof. However, the disclosure is not limited to particular methods of detection.

The availability of antibodies specific for CTIP2 facilitates the detection and quantitation of CTIP2 proteins. Exemplary immunoassay methods are presented in Harlow and Lane (*Antibodies, A Laboratory Manual*, CSHL, New York, 1988), Bancroft and Stevens (*Theory and Practice of Histological Techniques*, Churchill Livingstone, 1982) and Ausubel et al. (*Current Protocols in Molecular Biology*, John Wiley & Sons, New York, 1998). One specific, non-limiting example of an anti-CTIP2 antibody is a rat anti-CTIP2 antibody (Abcam, Cambridge, Mass.; product number 18465; clone 25B6). CTIP2 antibodies are also commercially available from Santa Cruz Biotechnology, Santa Cruz, Calif.; and Bethyl Laboratories, Montgomery, Tex. One-specific non-limiting example of an anti-CTIP2 antibody is a rabbit Bcl11b antibody (Bethyl Laboratories, Montgomery, Tex.), reactivity with human and mouse Bcl11b is expected owing to complete identify between this ortholog and human Bcl11b at the site to which the epitope maps.

Generally, the method includes contacting a biological sample obtained from a subject (such as a sample containing head and neck cells or proteins isolated from such a sample) with a CTIP2-specific antibody under conditions sufficient for the antibody to specifically bind to CTIP2 proteins in the sample, thereby forming CTIP2-antibody complexes. The resulting CTIP2-antibody complexes are then detected using any standard detection system. For example, the CTIP2-antibody can include a label, thereby permitting detection of the complexes. In some examples, the CTIP2-antibody complexes are contacted with an appropriate labeled secondary antibody under conditions sufficient to permit specific binding of the secondary antibody to CTIP2-antibody complexes, thereby forming labeled CTIP2-antibody complexes. The label associated with the secondary label can then be detected. Similar methods can be used to detect CTIP2 localization patterns in cells obtained from the subject. In one example, cells obtained from a subject can also be used to detect CTIP2 localization patterns.

Methods for labeling antibodies so that they can be detected are well known. Exemplary labels include fluorophores, such as Cy3, FITC, BODIPY, and Cy5. Methods of detecting labels are known, and include detection using spectroscopy, microscopy and flow cytometry.

In some examples, the biological sample includes proteins isolated from a tissue biopsy or cell sample. In one example, the biological sample includes proteins isolated from a head and neck cell sample. In other examples, the biological sample includes proteins isolated from a breast, lung, prostate, cervical or ovarian sample.

K. Detecting CTIP2 Nucleic Acid Molecule Expression

Methods of detecting a target nucleic acid molecule (such as CTIP2 RNA or DNA, for example mRNA or cDNA) in a sample are well known in the art. For example, nucleic acid amplification methods (with the appropriate probes and primers), as well as nucleic acid arrays (containing the appropriate probes), can be used. For example, the level of CTIP2 gene expression can be determined or even quantitated utilizing methods well known in the art, such as Northern-Blots, RNase protection assays, nucleic acid arrays, quantitative PCR (such as TaqMan assays), dot blot assays, in-situ hybridization, or combinations thereof.

In one example, the method includes contacting nucleic acid molecules (which can be isolated) from a biological sample obtained from a subject (such as a sample containing head and neck cells or nucleic acid molecules obtained from such a sample) with a CTIP2-specific nucleic acid probe under conditions sufficient for the probe to specifically bind to CTIP2 nucleic acid molecules (such as mRNA molecule) in the sample, thereby forming CTIP2-nucleic acid molecules complexes. The resulting complexes are then detected using any standard detection system, for example by detecting a label on the probe.

In another example, the method includes contacting nucleic acid molecules (which can be isolated) from a biological sample obtained from a subject (such as a sample containing head and neck cells or nucleic acid molecules obtained from such a sample) with primers that permit amplification of CTIP2. The resulting amplicons can be detected, for example by detecting a label on the amplicon. In a specific example, the amplicons are applied to a nucleic acid molecule detection array containing CTIP2-specific nucleic acid probes that can hybridize specifically to the amplicons, under suitable hybridization conditions to form a hybridization complex. The hybridization conditions are selected to permit discrimination between matched and mismatched oligonucleotides. Hybridization conditions can be chosen to correspond to those known to be suitable in standard procedures for hybridization to filters and then optimized for use with the arrays. For example, conditions suitable for hybridization of one type of target are adjusted for the use of other targets (such as a control sequence) for the array. In particular, temperature is controlled to substantially eliminate formation of duplexes between sequences other than exactly complementary CTIP2 sequences.

A variety of known hybridization solvents can be employed, the choice being dependent on considerations known to one of skill in the art (see U.S. Pat. No. 5,981,185). Detecting a hybridized complex in an array of oligonucleotide probes has been previously described (see U.S. Pat. No. 5,985,567). In one example, detection includes detecting one or more labels present on the oligonucleotides, the sequences obtained from the subject, or both. Detection can further include treating the hybridized complex with a conjugating solution to effect conjugation or coupling of the hybridized complex with the detection label, and treating the conjugated, hybridized complex with a detection reagent. In particular examples, the method further includes quantification, for instance by determining the amount of hybridization.

Methods for labeling nucleic acid molecules so that they can be detected are well known. Examples of such labels include non-radiolabels and radiolabels. Non-radiolabels include, but are not limited to enzymes, chemiluminescent compounds, fluorophores, metal complexes, haptens, colorimetric agents, dyes, or combinations thereof. Radiolabels include, but are not limited to, $^{32}P$ and $^{3}H$. Radioactive and fluorescent labeling methods, as well as other methods known in the art, are suitable for use with the present disclosure. In one example, the primers used to amplify the subject's nucleic acids are labeled (such as with biotin, a radiolabel, or a fluorophore). In another example, the amplified nucleic acid samples are end-labeled to form labeled amplified material. For example, amplified nucleic acid molecules can be labeled by including labeled nucleotides in the amplification reactions. In another example, nucleic acid molecules obtained from a subject are labeled, and applied to an array containing oligonucleotides.

L. Arrays

In particular examples, methods of detecting or diagnosing SCC involve detecting an increase in CTIP-2 expression. In some examples, additional SCC-related molecules are detected (such as at least one, at least two, at least three, at least four, at least five, at least 10 or at least 20 discussed in Section IVA-H, above), wherein differential expression (such as an increase or decrease in gene or protein expression) in any combination of at least four SCC-related molecules of the subject, indicates that the subject has SCC or has a particular stage of SCC.

In one non-limiting example, methods of detecting or diagnosing HNSCC involve detecting differential expression in any combination of at least four HNSCC-related molecules of the subject, such as any combination of a CTIP2-related molecule with at least three of the genes (or proteins) discussed in Section IVA-H, above. In another example, the method includes screening expression of one or more of a CTIP2-related molecule (for instance, CTIP2 (for instance, GenBank Accession Nos: NP_075049.1 and NM_022898.1), or CTIP2$_L$), and EGFR (for instance, GenBank Accession Nos: AAB19486.2 and NM_005228); Her-2/neu (for instance, GenBank Accession Nos: AAD56009.2 and AF177761.2); c-erbB 3-4 (for instance, GenBank Accession Nos: BAA07827.1 and Z23134.1); Cyclin D1 (for instance, GenBank Accession No: CAA54800.1); Ki67 (for instance, GenBank Accession Nos: CAD99007.1 and AJ567755.1); bcl-2 (for instance, GenBank Accession Nos: ABX60202.1 and AY220759.1); Fas (for instance, GenBank Ref. Nos: CAI13871.1 and M67454); p27 (for instance, GenBank Accession Nos: BAA25263.1 and NM_004064.2); p53 (for instance, GenBank Accession Nos: BAC16799.1 and AF307851); VEGF (for instance, GenBank Accession Nos: CAM28207.1 and AB021221); bFGF (for instance, GenBank Accession Nos: AAB21432.2 and NM_002006.4); PDGF-AB (for instance, GenBank Accession Nos: NP_002598.4 and NM_002608.1; PDGF-BB (for instance, GenBank Accession Nos: NP_148937.1 and NM_033016.1); G-CSF (for instance, GenBank Accession Nos: NP_757374.1 and NM_172220.1); GM-CSF (for instance, GenBank Accession Nos: AAA52578.1 and AAA52578.1); HIF1 (for instance, GenBank Accession Nos: Q16665.1 and NM_001530.2); HIF2 (for instance, GenBank Accession No: Q99814.3); MMP (for instance, GenBank Accession Nos: AAV28732.1 and NM_004530); TIMP (for instance, GenBank Accession Nos: CAA00898.1 and NM_000362.4); NY-ESO-1 (for instance, GenBank Accession No: CAA05908.1); MAGE-1 (for instance, GenBank Accession Nos: AAA03229.1 and NM_004988.4); MAGE-3 (for instance, GenBank Accession Nos: AAA17446.1 and NM_005362.3); galectin-3 (for instance, GenBank Accession Nos: NP_002297.2 and AK314929.1); EIF4G1 (for instance, GenBank Accession Nos: AAI40897.1 and NM_182917.3); DVL3 (for instance, GenBank Accession Nos: NP_004414.3 and NM_004423.3); EPHB4 (for instance, GenBank Accession Nos: EAL23820.1 and NM_004444.4); MCM7 (for instance, GenBank Accession Nos: AAH09398.1 and NM_005916; BRMS1 (for instance, GenBank Accession Nos: CAG33454.1 and AK313773.1); SART1 (for instance, GenBank Accession Nos: NP_005137.1 and NM_005146.4); or a combination of SCC-related molecules that includes at least 1, at least 2, at least 3, at least 4, at least 5 or at least 6 of these molecules. For example, the method can include screening expression of CTIP2, along with other SCC-related molecules (such as any combination that includes at least 3 additional molecules (markers) listed in Section IVA-H). In a specific example, the method can include screening expression of CTIP2, along with other HNSCC-related molecules (such as any combination that includes at least 3 additional molecules (markers) listed in Section IVA-H). It is contemplated herein that all GenBank Accession Numbers as provided are incorporated by reference as of the filing date of the earliest provisional patent application.

Differential expression can be represented by increased or decreased expression in the at least one SCC-related molecule (for instance, a nucleic acid or a protein). For example, differential expression includes, but is not limited to, an increase or decrease in an amount of a nucleic acid molecule or protein, the stability of a nucleic acid molecule or protein, the localization of a nucleic acid molecule or protein, or the biological activity of a nucleic acid molecule or protein, for example a change of at least 2-, 3-, 4-, 5- or 10-fold relative to a corresponding normal (e.g., non-SCC) sample. Specific examples include evaluative methods in which changes in gene expression in at least four SCC-related nucleic acid molecules (or corresponding protein) are detected (for example nucleic acids or proteins obtained from a subject thought to have had or known to have had a SCC), such as changes in gene (or protein) expression in any combination of at least 3, at least 5, at least 10, at least 15, at least 20, at least 25, at least 50, at least 100, or more SCC-related molecules. In one embodiment, evaluative methods include changes in gene expression in at least four HNSCC-related nucleic acid molecules (or corresponding protein), detected in a sample from a subject thought to have had or known to have had a HNSCC, such as changes in gene (or protein) expression in any combination of at least 3, at least 5, at least 10, at least 15, at least 20, at least 25, at least 50, at least 100, or more HNSCC-related molecules.

In particular examples a change in expression is detected in a subset of HNSCC-related molecules (such as nucleic acid sequences or protein sequences) that selectively evaluate HNSCC, for example to determine the grade or stage of the disease. In another example, a change in expression is detected in a subset of SCC-related molecules that selectively evaluate (e.g., determine the grade or stage of the disease) in a prostate, lung, breast, cervical or ovarian SCC. In one example, the subset of molecules can include a set of any combination of CTIP2 and three other SCC-related genes listed in Section IVA-H.

In particular examples, methods for detecting a change in expression in CTIP2 and the other disclosed SCC-related genes listed in Section IVA-H, above, use the arrays disclosed herein. In one example, methods for detecting a change in expression in CTIP2 and disclosed HNSCC-related genes listed in Section IVA-H, use the arrays disclosed herein. Arrays can be used to detect the presence of sequences whose expression is upregulated or downregulated in response to SCC, such as sequences listed in Section IVA-H, for example using specific oligonucleotide probes or antibody probes. The arrays herein termed "SCC detection arrays," are used to evaluate SCC, for example to determine whether a subject has a SCC, determine the grade or stage of the disease, predict the likelihood of recovery of a subject who has a SCC, to identify an appropriate therapy for a subject who has a SCC, or combinations thereof. Additionally, arrays herein termed "HNSCC detection arrays," are used to evaluate HNSCC, for example to determine whether a subject has HNSCC, determine the grade or stage of the disease, predict the likelihood of recovery of a subject who has HNSCC, to identify an appropriate therapy for a subject who has HNSCC, or combinations thereof.

In particular examples, the disclosed arrays can include nucleic acid molecules, such as DNA or RNA molecules, or antibodies.

Nucleic Acid Arrays

In one example, the array includes nucleic acid oligonucleotide probes that can hybridize to CTIP2, and for example one or more positive or negative controls (such as housekeeping genes), and in some examples additionally at least three of the SCC-related gene sequences listed in Section IVA-H. For example, the array can include nucleic acid oligonucleotide probes that can hybridize to any combination of CTIP2, at least one positive or negative control, and/or at least three HNSCC-related gene sequences listed in Section IVA-H. In particular examples, an array includes oligonucleotides that can recognize CTIP2 and all of the HNSCC-associated genes listed in Section IVA-H, above. Certain of such arrays (as well as the methods described herein) can include other SCC-related molecules known in the art.

In a specific example, an array includes oligonucleotide probes that can recognize a CTIP2-related molecule (for instance, CTIP2, or $CTIP2_L$); and at least one or more of EGFR; Her-2/neu; c-erbB 3-4; AMACR; CA 15-3; CA-125; CEA; Cyclin D1; CYFRA; Ki67; bcl-2; Brn-3a; Fas; hTERT; p27; p53; p63; proGRP; VEGF; bFGF; PDGF-AB; PDGF-BB; G-CSF; GM-CSF; HIF1; HIF2; MCM; MMP; NSE; TIMP; TPA; NY-ESO-1; M-CSF; MAGE-1; MAGE-3; cytokeratin-5; cytokeratin 6; galectin-3; EIF4G1; DVL3; EPHB4; MCM7; BRMS1; SART1; SCC-Ag; or a combination of HNSCC-related molecules that includes at least 1, at least 2, at least 3, at least 4, at least 5 or at least 6 of these molecules.

In one example, a set of oligonucleotide probes is attached to the surface of a solid support for use in detection of HNSCC-associated sequences. Additionally, if an internal control nucleic acid sequence is used (such as a nucleic acid sequence obtained from a head/neck cell or tissue sample from a subject who does not have HNSCC) an oligonucleotide probe can be included to detect the presence of this control nucleic acid molecule.

The oligonucleotide probes bound to the array can specifically bind or hybridize sequences obtained from the subject, or amplified from the subject (such as under high stringency conditions). Thus, sequences of use with the method are oligonucleotide probes that recognize SCC-related sequences, such as gene sequences (or corresponding proteins) listed in Section IVA-H. In one example, sequences of use with the method are oligonucleotide probes that recognize HNSCC-related sequences, such as gene sequences or corresponding proteins listed in Section IVA-H. Such sequences can be determined by examining the sequences of the different species, and choosing oligonucleotide sequences that specifically anneal to a particular HNSCC-related sequence, but not others. One of skill in the art can identify other HNSCC-associated oligonucleotide molecules that can be attached to the surface of a solid support for the detection of other HNSCC-associated nucleic acid sequences.

The methods and apparatus in accordance with the present disclosure takes advantage of the fact that under appropriate conditions oligonucleotides form base-paired duplexes with nucleic acid molecules that have a complementary base sequence. The stability of the duplex is dependent on a number of factors, including the length of the oligonucleotides, the base composition, and the composition of the solution in which hybridization is effected. The effects of base composition on duplex stability can be reduced by carrying out the hybridization in particular solutions, for example in the presence of high concentrations of tertiary or quaternary amines.

The thermal stability of the duplex is also dependent on the degree of sequence similarity between the sequences. By carrying out the hybridization at temperatures close to the anticipated $T_m$'s of the type of duplexes expected to be formed between the target sequences and the oligonucleotides bound to the array, the rate of formation of mismatched duplexes may be substantially reduced.

The length of each oligonucleotide sequence employed in the array can be selected to optimize binding of SCC-associated nucleic acid sequences. An optimum length for use with a particular SCC-associated nucleic acid sequence under specific screening conditions can be determined empirically. Thus, the length for each individual element of the set of oligonucleotide sequences included in the array can be optimized for screening. In one example, oligonucleotide probes are from about 20 to about 35 nucleotides in length or about 25 to about 40 nucleotides in length. In another example, the oligonucleotide sequence employed in the array is selected from a prostate, lung, head and neck, breast, cervical, or ovarian-associated nucleic acid sequence.

The oligonucleotide probe sequences forming the array can be directly linked to the support. Alternatively, the oligonucleotide probes can be attached to the support by non-SCC-associated sequences such as oligonucleotides or other molecules that serve as spacers or linkers to the solid support.

Protein Arrays

In another example, an array includes protein sequences (or a fragment of such proteins, or antibodies specific to such proteins or protein fragments), which include CTIP2 and for example one or more positive or negative controls (such as housekeeping proteins), and in some examples additionally at least three of the SCC-related protein sequences listed in Section IVA-H, above. In particular examples, an array includes proteins that can recognize all SCC-associated proteins listed in Section IVA-H, above. In one non-limiting example, an array includes protein sequences or a fragment thereof, or antibodies specific to the proteins or protein fragments, which include CTIP2 and at least three HNSCC-related protein sequences as provided in Section IVA-H. In particular examples, an array includes proteins that recognize all HNSCC-associated proteins listed in Section IVA-H. Such arrays can also contain any particular subset of these sequences. For example, an array can include probes that can recognize a CTIP2-related sequence (for instance, CTIP2 or $CTIP2_L$), and for example one or more positive or negative controls (such as housekeeping proteins), and in some examples additionally and EGFR; Her-2/neu; c-erbB 3-4; AMACR; CA 15-3; CA-125; CEA; Cyclin D1; CYFRA; Ki67; bcl-2; Brn-3a; Fas; hTERT; p27; p53; p63; proGRP; VEGF; bFGF; PDGF-AB; PDGF-BB; G-CSF; GM-CSF; HIF1; HIF2; MCM; MMP; NSE; TIMP; TPA; NY-ESO-1; M-CSF; MAGE-1; MAGE-3; cytokeratin-5; cytokeratin 6; galectin-3; EIF4G1; DVL3; EPHB4; MCM7; BRMS1; SART1; SCC-Ag; or a combination of HNSCC-related proteins that includes at least 1, at least 2, at least 3, at least 4, at least 5 or at least 6 of these proteins.

The proteins or antibodies forming the array can be directly linked to the support. Alternatively, the proteins or antibodies can be attached to the support by spacers or linkers to the solid support.

Changes in expression of SCC-related proteins can be detected using, for instance, a SCC-specific binding agent, which in some instances is labeled with an agent that can be detected. In certain examples, detecting a change in protein expression includes contacting a protein sample obtained from a subject with a SCC-specific binding agent (which can be for example present on an array); and detecting whether the binding agent is bound by the sample and thereby measuring the level of SCC-related protein present in the sample. A difference in the level of SCC-related protein in the sample, relative to the level of SCC-related protein found in an analogous sample from a subject who does not have a SCC, such as a change of at least 2-fold, 3-, 4-, 5-, 10-, or 15-fold, in particular examples indicates that the subject has a SCC.

In one example, detecting a change in protein expression includes contacting a protein sample obtained from a breast sample with a breast SCC-specific binding agent on an array; and detecting whether the binding agent is bound by the breast sample and thereby measuring the level of breast SCC-related protein in the sample. A difference in the level of breast SCC-related protein in the sample, such as a change of at least 2-fold, 3-, 4-, 5-, 10-, or 15-fold, relative to the level of a breast SCC-related protein found in an analogous sample from a subject who does not have a breast SCC, in particular examples indicates that the subject has a breast SCC. It is contemplated herein that the method for determining the change in expression of a SCC-related protein is equally applicable to all forms of SCC. In particular examples, the method is particularly suitable for determining the change in expression of a SCC-related protein, when the SCC is a prostate, lung, cervical, breast or ovarian SCC.

Solid Support

The solid support can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulformes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides are not amenable to non-specific binding, or when non-specific binding occurs, such materials can be readily removed from the surface without removing the oligonucleotides.

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. Particularly disclosed for the preparation of arrays at this time is biaxially oriented polypropylene (BOPP) films; in addition to their durability, BOPP films exhibit low background fluorescence.

The array formats of the present disclosure can be included in a variety of different types of formats. A "format" includes any format to which the solid support can be affixed, such as microtiter plates, test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217: 306-10, 1994. In one example, the oligonucleotides are synthesized onto the support using conventional chemical techniques for preparing oligonucleotides on solid supports (such as see PCT applications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

M. Reference Values and Samples

In some examples, the detected CTIP2 protein or nucleic acid can be compared to a reference value (such as a number or range of values) or reference sample (such as an actual biological sample). A comparison to a reference sample or value representing a level of CTIP2 expression expected for normal (non-cancerous, non-dysplastic) tissue or a particular disease state, such as dysplasia or SCC (or a particular stage thereof), can be used to determine if the subject from whom the sample was obtained has dysplasia or a SCC. In one embodiment, a reference sample or value representing a level of CTIP2 expression expected for normal head and neck tissue, or a particular disease state such as HNSCC, can be used to determine if the subject from whom the sample was obtained has HNSCC.

In one example, the reference value or sample represents a relative or actual amount of CTIP2 expression expected or routinely observed for normal (non-dysplastic, non cancerous) tissue. In another example, the reference value or sample represents a relative or actual amount of CTIP2 expression expected or routinely observed for dysplasia or a particular grade thereof. In another example, the reference value or sample represents a relative or actual amount of CTIP2 expression expected or routinely observed for SCC or a particular grade thereof (such as Stage 0, Stage I, Stage II, Stage III, or Stage IV, or a substage thereof such as Stage IIA). In some examples, one or more of such reference value or samples are used, such as at least 2, at least 5, at least 10 of such reference values or samples, for example, 1, 2, 3, 4, 5, 6, 7, 8, 9, 10, 11, 12, 13, 14, 15 or 16 of such reference values or samples.

In some examples, the reference sample or value represents a CTIP2 localization pattern expected for normal tissue or a particular disease state, such as dysplasia or SCC (e.g., prostate SCC or a particular stage thereof). In one example, the reference value or sample represents a relative or actual CTIP2 (or $CTIP2_L$) localization expected or routinely observed for normal (non-dysplastic, non cancerous) head and neck tissue. In another example, the reference value or sample represents a relative or actual CTIP2 (or $CTIP2_L$) localization expected or routinely observed for dysplasia or a particular grade thereof. In another example, the reference value or sample represents a relative or actual CTIP2 (or $CTIP2_L$) localization expected or routinely observed for SCC or a particular grade thereof (such as Stage 0, Stage I, Stage II, Stage III, or Stage IV, or a substage thereof such as Stage IIA). In some examples, one or more of such reference value or samples are used, such as at least 2, at least 5, at least 10 of such reference values or samples, for example, 1, 2, 3, 4, 5, 6, 7, 8, 9, 10, 11, 12, 13, 14, 15 or 16 of such reference values or samples.

In some examples, reference values or samples representing CTIP2 (or $CTIP2_L$) expression and reference value or samples representing CTIP2 (or $CTIP2_L$) localization patterns are used.

N. Exemplary Methods for Immunohistochemical Staining of Tissue with CTIP2-Specific Antibodies Immunohistochemistry (IHC) is a well-known method and variations on such methods are readily determined with routine experimentation by those of ordinary skill in the art (see, e.g., Dabbs, *Diagnostic Immunohistochemistry*, Churchill Livingstone, 2002). Exemplary methods for detecting CTIP2 (or other SCC-associated protein) expression in tissue by manual IHC using an antigen-binding molecule specific for CTIP2 or $CTIP2_L$ are provided in Table 1. One skilled in the art will recognize that similar methods provided in the Table below can be used for diagnostic specific binding reagents for other SCC-related markers. It is contemplated herein that the method for detecting CTIP2 expression in tissue by IHC is equally applicable to all forms of SCC. In particular examples, the methods for detecting CTIP2 expression are particularly suited for prostate, lung, cervical, breast or ovarian SCCs.

TABLE 1

Exemplary IHC Methods

| Step # | Manual IHC Assay |
|---|---|
| 0 | Fresh tissue is placed in a fixative (such as, 10% neutral buffered formalin) for approximately 12-48 hours at room temperature. Then, the tissue is dehydrated through graded alcohols (e.g., 50% to 70% to 90% to 95% to 100% EtOH) for 1-2 hours at each grade, and infiltrated with a clearing reagent (such as, xylene) for 3-5 hours at room temperature. The cleared tissue is placed in melted (approximately 63° C.) paraffin for 3-6 hours. Samples are removed and embedded in paraffin blocks for subsequent microtome sectioning. 3-10 μm sections are cut and placed on glass slides. |
| 1 | Deparaffinize tissue sections in xylene; then, rehydrate through graded alcohols to distilled water. |
| 2 | Place tissue sections in 0.5% v/v hydrogen peroxide/methanol for approximately 10 minutes. |
| 3 | Pretreat slides for antigen retrieval using an appropriate method (e.g., high-temperature antigen unmasking, trypsin, etc.) if required. |
| 4 | Wash slides with distilled water for approximately 5 minutes. |
| 5 | Wash slides in saline buffer (e.g., PBS, TBS) for approximately 5 minutes. |
| 6 | Cover tissue sections with blocking reagent (e.g., 10% v/v normal rabbit serum in buffer) for approximately 10 minutes. |
| 7 | Remove excess blocking reagent and replace with primary antibody (e.g., rabbit monoclonal antibody or mouse monoclonal antibody) diluted in blocking reagent as required for approximately 60 minutes at 25° C. or overnight at 4° C. |
| 8 | Wash twice in buffer for approximately 5 minutes per wash. |
| 9 | Remove excess buffer and incubate tissue sections with biotinylated secondary antibody (e.g., biotinylated rabbit anti-mouse antibody or biotinylated goat anti-rabbit antibody as appropriate for the subject primary antibody) diluted in blocking reagent for 30 minutes at 25° C. |
| 10 | Wash twice in buffer for approximately 5 minutes per wash. |
| 11 | Remove excess buffer and incubate tissue sections with streptavidin-horse radish peroxidase (HRP) conjugate for 30 minutes at 25° C. |
| 12 | Wash twice in buffer for approximately 5 minutes per wash. |
| 13 | Develop detectable color with 3,3'-diaminobenzidine tetrahydrochloride (DAB) at room temperature for approximately 5-10 minutes. |
| 14 | Rinse slides in water. |
| 15 | If desired, counterstain with hematoxylin (e.g., Carson, Histotechnology: A Self-Instructional Text, Chicago: ASCP Press, 1997). |
| 16 | Dehydrate, clear and mount coverslip on slides. |

IHC for the detection of antibodies specific for CTIP2 (or other SCC-associated protein) also can be performed on automated staining platforms, such as the BenchMark™ series 40 instruments manufactured by Ventana Medical Systems (Tucson, Ariz.).

Following IHC, staining intensity is scored, in certain examples, by light microscopy according to the following criteria:

TABLE 2

Scoring of Immunohistochemical Staining

| Report Result | Staining Intensity Score | Microscope Observation |
|---|---|---|
| Positive: In case CTIP2 over-expression is detected, it will appear as specific brown to black nuclear staining of tumor cells (depending on tumor stage), with or without cytoplasmic staining, after incubation with primary antibody. | 3+ | Strong reactivity: Dark brown to black strong nuclear staining is usually observed in most of the tumor cells. Cytoplasmic reactivity may be absent or may be moderately present in certain places. |
| | 2.5 | Intense reactivity: Shades of brown nuclear staining of medium darkness (intensity). Cytoplasmic reactivity of moderate intensity may be seen in certain places |
| | 2+ | Moderate reactivity: Shades of brown nuclear staining of intermediate darkness (intensity). Cytoplasmic reactivity of moderate intensity is also considered 2+. The cytoplasmic reactivity is of weaker intensity. |
| | 1.5 | Slight reactivity: Staining of intermediate intensity that is nuclear. Cytoplasmic reactivity that is uniform and involves all the cytoplasm may be present, but should not be evaluated for positivity. |
| | 1+ | Weak reactivity: Faint or light brown reactivity that is nuclear. Cytoplasmic reactivity that is uniform and involves all the cytoplasm may be present, but should not be evaluated for positivity. |

TABLE 2-continued

Scoring of Immunohistochemical Staining

| Report Result | Staining Intensity Score | Microscope Observation |
|---|---|---|
| Negative: Absence of nuclear staining above background in all tumor cells. Presence of cytoplasmic in the absence of nuclear staining. | 0.5 | Trace reactivity: Trace brown reactivity where cytoplasmic localization is indeterminate. |
| | 0 | No reactivity |

O. Methods of Screening for CTIP2 Inhibitors

Disclosed herein are methods of screening for CTIP2 inhibitors. These screening methods include, but are not limited to, methods employing solid phase, liquid phase, cell-based or virtual (in silico) screening assays. In one exemplary assay, compounds that affect (e.g., decrease) CTIP2 expression or function are identified. For instance, certain assays identify compounds that modulate (e.g., decrease) the expression of a CTIP2-encoding nucleic acid (e.g., DNA or mRNA) or CTIP2 polypeptide, or that affect a CTIP2 gene regulatory sequence so as to modify (e.g., decrease) CTIP2 gene (and/or mRNA) expression. Compounds identified via assays such as those described herein are useful, for example, in decreasing CTIP2 expression or function.

CTIP2 polypeptides and CTIP2-encoding nucleic acid sequences have been described in detail elsewhere herein. In addition, it is to be understood that disclosed methods involving the detection (or determination) of a change, modification, alteration, etc. (e.g., decrease) in a particular composition or process, typically, are intended to be relative to a known or determined standard and/or control state, for example, as existed in the same test system prior to the addition of a test agent, or as existed in a comparable test system in the absence of a test agent.

Some of the disclosed methods are methods of screening for agents that affect CTIP2 gene expression. For instance, certain methods are methods of identifying agents that modulate the expression of a CTIP2-encoding nucleic acid or a reporter gene operably linked to a CTIP2 transcriptional regulatory sequence. Generally, such methods involve contacting (directly or indirectly) with a test agent an expression system that includes a nucleic acid sequence encoding a CTIP2 polypeptide, or a reporter gene operably linked to a CTIP2 transcription regulatory sequence, and detecting a change (e.g., a decrease) in the expression of the CTIP2-encoding nucleic acid or reporter gene.

Modulation of the expression of a CTIP2 gene or gene product (e.g., transcript or protein) can be determined using any expression system capable of expressing a CTIP2 polypeptide or transcript (such as, a cell, tissue, or organism, or in vitro transcription or translation systems). In some embodiments, cell-based assays are performed. Non-limiting exemplary cell-based assays may involve test cells such as, cells (including cell lines) that normally express a CTIP2 gene, its corresponding transcript(s) and/or CTIP2 protein(s), or cells (including cell lines) that have been transiently transfected or stably transformed with a reporter construct driven by a regulatory sequence of a CTIP2 gene.

As mentioned above, some disclosed methods involve cells (including cell lines) that have been transiently transfected or stably transformed with a reporter construct driven by a regulatory sequence of a CTIP2 gene. A "regulatory sequence" as used herein can include some or all of the regulatory elements that regulate the expression of a particular nucleic acid sequence (such as, a CTIP2 gene) under normal circumstances. In particular examples, a regulatory region includes the contiguous nucleotides located at least 100, at least 500, at least 1000, at least 2500, at least 5000, or at least 7500 nucleotides upstream of the transcriptional start site of the regulated nucleic acid sequence (such as, a CTIP2 gene).

CTIP2 gene regulatory regions are provided for a variety of species (including non-primate, or non-primate, mammalian species) in publicly available genomic sequences. For example, human CTIP2 is located on human chromosome 14 at location 14q32.2 (GenBank Accession No. NM_022898, herein incorporated by reference as of Jun. 26, 2008). Accordingly, a nucleic acid sequence of an upstream (i.e., 5') regulatory region of the human CTIP2 gene can include at least 100, at least 500, at least 1000, at least 2500, at least 5000, at least 7500, or at least 10,000 nucleotides upstream of the CTIP2 sequence in GenBank NM_022898.

In method embodiments involving a cell transiently or stably transfected with a reporter construct operably linked to a CTIP2 regulatory region, the level of the reporter gene product can be measured. Reporter genes are nucleic acid sequences that encode readily assayed proteins. Numerous reporter genes are commonly known and methods of their use are standard in the art. Non-limiting representative reporter genes are luciferase, β-galactosidase, chloramphenicol acetyl transferase, alkaline phosphatase, green fluorescent protein, and others. In the applicable methods, the reporter gene product is detected using standard techniques for that particular reporter gene product (see, for example, manufacturer's directions for human placental alkaline phosphatase (SEAP), luciferase, or enhanced green fluorescent protein (EGPF) available from BDBiosciences (Clontech); or galactosidase/luciferase, luciferase, or galactosidase available from Applied Biosystems (Foster City, Calif., USA); or available from various other commercial manufacturers of reporter gene products). A difference (such as an at least 20%, 40%, 50%, 75%, 80% or 95% decrease) in the level and/or activity of reporter gene measured in cells in the presence or absence of a test agent indicates that the test agent modulates (e.g., decreases) the activity of the CTIP2 regulatory region driving the reporter gene.

Suitable methods and materials for the practice or testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification (see, for instance, Sambrook et al., *Molecular Cloning: A Laboratory Manual*, 2d ed., Cold Spring Harbor Laboratory Press, 1989;

Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999).

EXAMPLES

Example 1

Material and Methods

This Example provides general materials and methods that were used for carrying out the experiments described below in Example 2. Although specific procedures are described, one of skill in the art will know that modifications can be made and other methods can be substituted.
Tissue Samples Paraffin embedded tissue (n=40) sections and cDNAs (n=28) from different HNSCC tumor samples and the corresponding histological normal tissues were obtained from Joseph Abecassis, Ph.D. Normal samples were collected from the farthest margin of the surgical resections (uvula).
Immunohistochemistry Formalin-fixed and paraffin-embedded HNSCC sections were used, and were provided by Joseph Abecassis, Centre Paul Strauss, Strasbourg, France. The sections were deparaffinized in xylene, dehydrated through graded alcohols, and placed in 0.1% hydrogen peroxide to quench any endogenous peroxidase activity. A 5 minute, 750 Watt microwave pretreatment in citrate buffer (pH 6.0) was repeated four times and followed by treatment with 10% normal rabbit serum for 30 minutes to block nonspecific antibody binding. The slides were then incubated with an anti-rat CTIP2 monoclonal antibody, 1/300 dilution (Abcam product number 18465; clone 25B6) in a humid chamber at 4° C. overnight. Secondary antibody staining was carried out with a biotin-labeled rabbit anti-rat antibody 1/500 dilution (Jackson Immuno Research Laboratories, INC, catalogue number: 112-065-143) for 2 hours at 37° C., followed by incubation with a streptavidin-biotin horseradish peroxidase complex (Vector Laboratories, catalog number: SA-5704). Detection was performed using DAB+ substrate (Vector: peroxide substrate kit, SK-4100) for 10 minutes. Counterstaining was performed with Mayer hematoxylin before dehydration and mounting. The expression of CTIP2 was analyzed by comparing the staining intensities of different samples with and without addition of primary antibody. The analysis of CTIP2 expression was performed independently by two investigators. Staining intensities for each section were as follows: 0=no staining; 1=weak staining; 2=moderate staining; and 3=strong staining. A tumor was considered CTIP2-positive if more than 10% of the tumor cells demonstrated positive nuclear staining.
Statistical Analysis The means and standard errors of QRT-PCR data among different samples were calculated, and the differences between them were determined by either T-test or 1 way anova, where p<0.05 was regarded as significant.
Quantitative Real Time PCR (QRT-PCR)

Reverse transcription was performed as described (Seghatoleslam, et al., (2006) *Biochem and Biophys Res Comm* 339:422-429). Briefly, reverse transcription was performed using 1 μg total RNA, random primers, and the superscript II RT-PCR system (Life Technologies). QPCR was performed on 1/50 dilutions of the CDNA samples using SYBR Green Supermix (Qiagen) in a Applied Biosystems 7500 Real-Time PCR system as described (Indra, et al., (2005) *Dev Biol* 285: 28-37). All reactions were performed in triplicate. Melting curve analyses were performed to ensure the specificity of QRT-PCR. Primer sets were used to test the expression of two forms of CTIP2 as shown in Table 3, and were designed using Primer3 Software. Data analysis was performed using the 2-ΔΔCt method described previously (Li, et al., (2004) *Clin Cancer Res* 10:8442-8450). Ribosomal phosphor-protein PO(RPLPO) was used as the reference gene. QRT-PCR-based gene expression values between the groups were compared by t-test or 1 way anova.

TABLE 3

Primers used for Real Time QRT-PCR

| CTIP2$_L$ (hCTIP2 E2-E3) | |
|---|---|
| Forward primer<br>ATCTGTCCCAAGCAGGAGAA | (SEQ ID NO: 1) |
| Reverse primer<br>GTCTGACCCTCACCCTGAGT | (SEQ ID NO: 2) |
| CTIP2 (hCTIP2 E2-E4) | |
| Forward primer<br>AGCAGGAGAACATTGCAGGTA | (SEQ ID NO: 3) |
| Reverse primer<br>GGAAATTCATGAGCGGGACT | (SEQ ID NO: 4) |

Example 2

CTIP2 is a Marker for Head and Neck Squamous Cell Carcinoma

This Example describes CTIP2 expression in HNSCC samples and the correlation between CTIP2 expression levels and disease state, as well as the use of CTIP2 expression as a marker for HNSCC.

To localize CTIP2, immunohistochemistry was performed using an antibody described earlier (Golonzhka, et al., (2007) *Gene Expr Patterns* 7:754-760). Paraffin-embedded sections of HNSCC and normal samples were obtained, and a high heat antigen retrieval technique was used to detect CTIP2 in paraffin-fixed sections from tumors (n=40), and adjacent normal tissue (n=8). Positive staining for CTIP2 was found to be exclusively nuclear. For head and neck adjacent normal tissue, staining was weaker than tumors, and also restricted to the basal layer keratinocytes (FIG. 1A). In dysplasia, CTIP2 expression was stronger than normal and extended to differentiated cell layers (FIG. 1B and FIG. 2A).

In well-differentiated tumors, CTIP2 staining was found to be restricted to the basal layers at the periphery of the carcinamatous clusters, and the staining was weaker (FIG. 1C). Stronger and homogeneous expression of CTIP2 was observed in moderately/poorly-differentiated tumors (FIGS. 1D-1F).

Figure 2A:
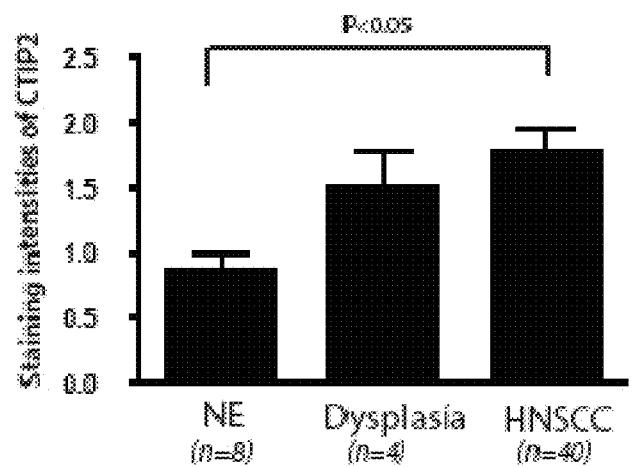
FIG. 2A is a graph showing the staining intensity of CTIP2 in normal epithelium (NE), dysplasia, and HNSCC. Mean measurements (±S.E.M) are shown. *p<0.05.
Figure 2B:
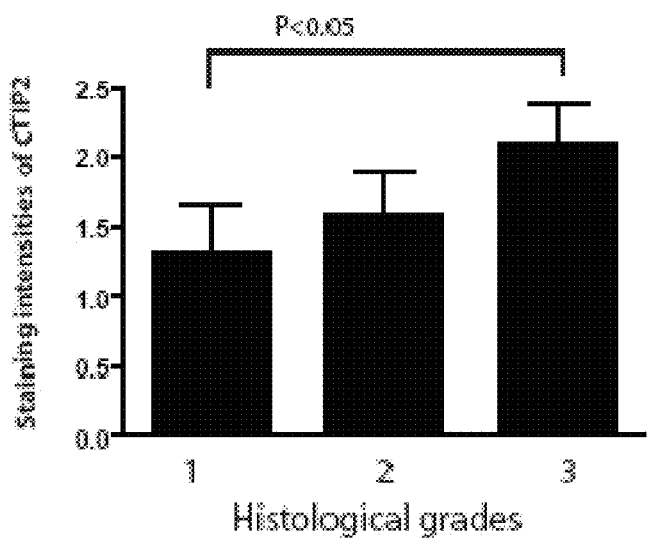
FIG. 2B is a graph showing staining intensities in different histological grades of HNSCC (well, moderate and poorly differentiated, respectively). Mean measurements (±S.E.M) are shown. *p<0.05.

The intensities of CTIP2 staining (0-3) were compared among the adjacent normal, dysplastic, and different histological grades of tumor (FIGS. 2A and 2B). Out of the 40 different samples that were analyzed, eight had adjacent normal epithelium, and four had dysplasia (FIG. 2A). Compared to normal epithelium, CTIP2 expression was strongly up-regulated in HNSCC samples (P<0.05; FIG. 2A). The strongest staining of CTIP2 (level 3) was observed in 11% of well-differentiated tumors, 25% of the moderately-differentiated tumors, and 58% of the poorly-differentiated tumors, compared to no staining of this intensity in adjacent normal epithelium (FIGS. 1 and 2). Overall, an increase in the intensity of CTIP2 expression, with the progression of carcinoma was observed in the samples (FIG. 2A). Thus, CTIP2 is overexpressed in HNSCC, and CTIP2 expression is linked to poor differentiation state of the tumor.

TABLE 4

Histological features of the HNSCC samples

| Number | Stage | Differentiation | Normal epithelium | Muscle | Salivary glands | Infiltrating lymphocytes |
|---|---|---|---|---|---|---|
| B5288 VI | 2 | Well | Yes | Yes | No | No |
| B5286 II | 3 | Well | Yes | Yes | Yes | No |
| B7992 II | 3 | Moderate | No | Yes | No | No |
| 34082 IV | 3 | Moderate | No | Yes | Yes | No |
| 24825 V | 3 | Moderate | Yes | Yes | No | No |
| 34088 II | 2 | Moderate | No | Yes | Yes | Yes |
| 22248 III | 2 | Poor | Yes | Yes | Yes | No |
| B13097 IV | 2 | Poor | Yes | Yes | No | Yes |
| 22246 II | 2 | Poor | Yes | Yes | Yes | Yes |

TABLE 5

Summary of CTIP2 expression as detected by immunohistochemistry using antigen retrieval method

| Number | Stage | Differentiation CTIP2 expression | Muscle | Salivary glands | Infiltrating lymphocytes |
|---|---|---|---|---|---|
| | | Well-differentiated | | | |
| B5288 VI | 2 | ++ | Negative | N/A | N/A |
| B5286 II | 3 | ++ | Negative | negative | N/A |
| | | Moderately-differentiated | | | |
| 24825 V | 3 | + | Negative | N/A | N/A |
| 34082 IV | 3 | +++ | Negative | Negative | N/A |
| 34088 II | 2 | +++ | Negative | Negative | +ve |
| B7992 II | 3 | +++ | Negative | N/A | N/A |
| | | Poorly-differentiated | | | |
| 22246 II | 2 | ++++ | Negative | Negative | ++ve |
| B13097 IV | 2 | ++ | Negative | N/A | Negative |
| 22248 III | 2 | ++++ | Negative | Negative | N/A |

Since CTIP2 has three different variants, and the antibody used in the above study could not detect the specific isoform by IHC, it was determined which isoform of CTIP2 is relevant to HNSCC disease progression. Human CTIP2 has 4 exons that encode one protein isoform generated by alternate splicing of exon 3 (FIG. 8). CTIP2 that includes all four exons is referred to herein as CTIP2 long ($CTIP2_L$), and the variant lacking exon 3 is referred to as CTIP2 (WT or native form (FIG. 8)). The variant lacking exon 2 and exon 3 is referred to herein as CTIP2 short.

To characterize the expression of CTIP2, quantitative real time PCR (QRT-PCR) and IHC was performed on RNA extracted from 28 different HNSCC samples. To distinguish between the isoforms of CTIP2, primers were chosen from exon 2 and exon 3 for $CTIP2_L$, and exon 2 and overlapping exon 2 and 4 for CTIP2 (FIG. 8). Both isoforms were amplified by PCR.

Figure 3A:
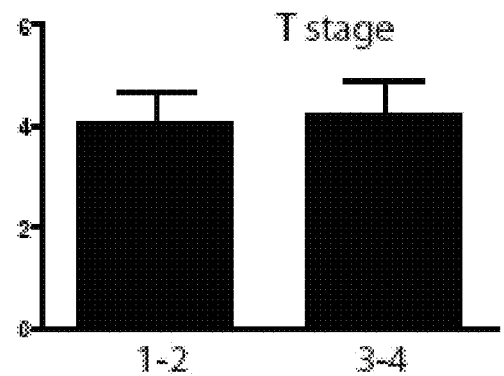
FIG. 3A is a graph showing the levels of expression of two transcripts of human CTIP2. The long form of CTIP2 ($CTIP2_L$) includes all 4 exons, and the normal form (wild-type) of CTIP2 lacks exon 3 (CTIP2). Primers for the long form were taken from exon 2 for the forward primer and from and exon 3 for the reverse primer, and for the CTIP2 form, the forward primer was taken from the boundary of exons 2 and 4, and the reverse primer from exon 4. Expression of the CTIP2 long form by QRT-PCR in HNSCC (n=28) is shown based on T stage (FIG. 3A), clinical stage (FIG. 3B), and differentiation status (FIG. 3C). The relative quantification levels are shown ±S.E.M. p values were not significant between the groups.
Figure 3B:
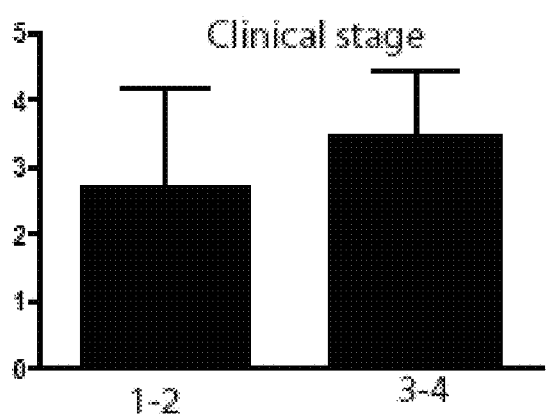
FIG. 3 includes three panels showing expression of CTIP2 long form by QRT-PCR in HNSCC.
Figure 3C:
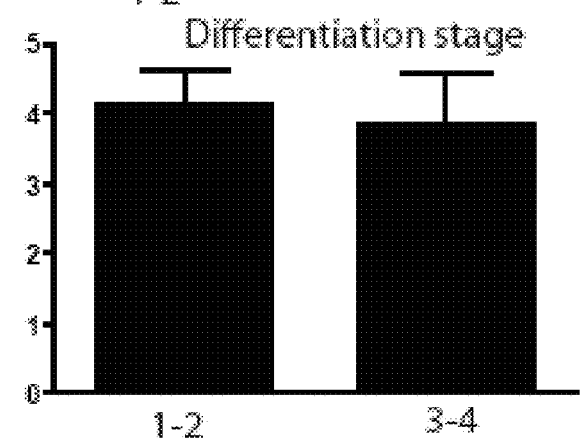
Figure 4A:
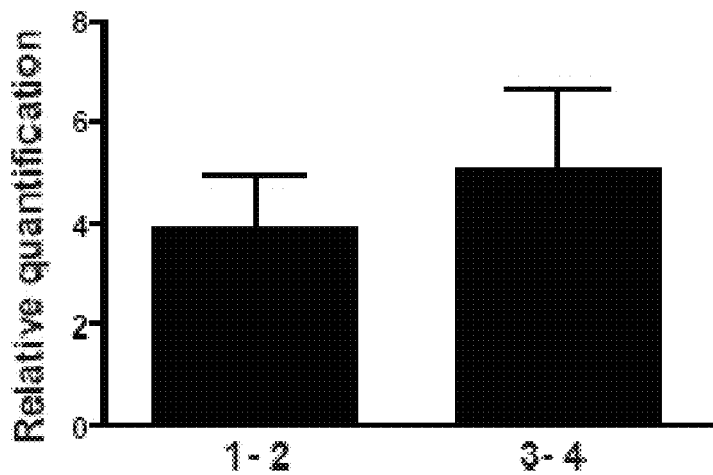
FIG. 4 includes three panels showing the clinico-pathological expression of CTIP2 by QRT-PCR in HNSCC (n=28). Expression of CTIP2 is shown based on T stage (FIG. 4A), clinical stage (FIG. 4B), and differentiation status (FIG. 4C). Relative quantification levels are shown ±S.E.M. Significant correlation of higher CTIP2 expression was observed with a poorer histological grade of the tumor, and a trend was noted in a relationship between expression and advanced T or clinical stage (P<0.05).
Figure 4B:
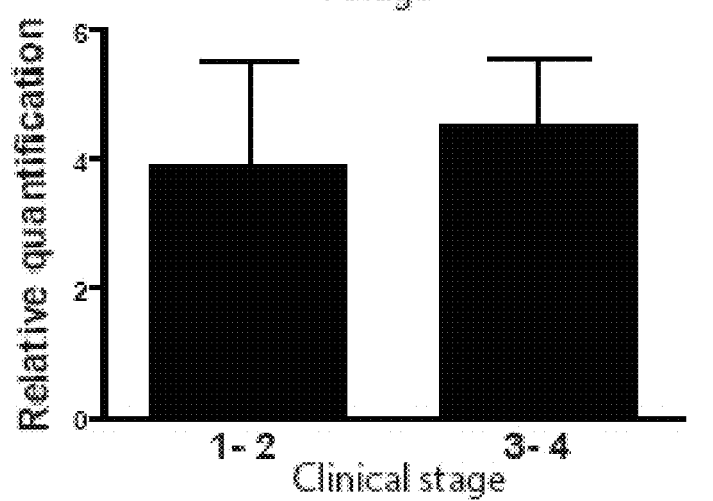
Figure 4C:
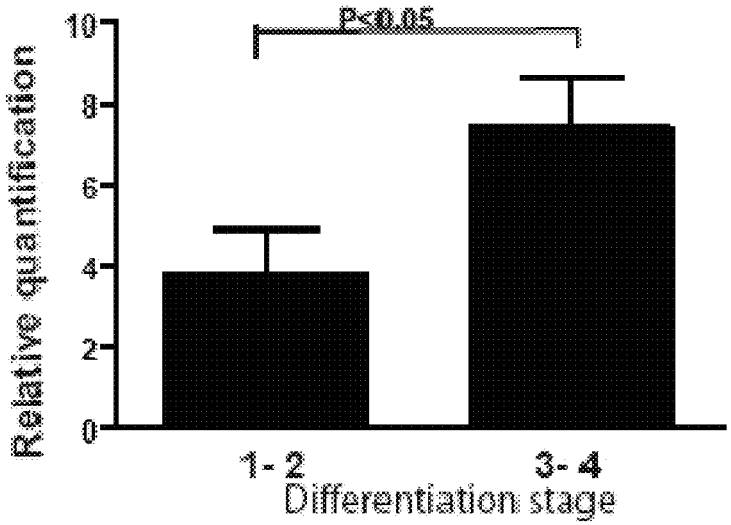

The samples from different tumor clinical stage and differentiation grades were divided into early cancer (1-2) and late cancer (3-4). A significant number of samples with normal to high mRNA expression were observed among patients with T1-T4 tumor size and with well, moderate to poor differentiation status, and regional metastasis. However, statistical studies showed no statistical significance of any correlation between mRNA expression and any of the clinicopathological parameters with the $CTIP2_L$ (FIG. 3 and Table 6). By comparison, there was a significant correlation of higher CTIP2 (CTIP2) expression with a poorer histological grade of the tumor, and a trend was noted in a relationship between expression and advanced T or clinical stage (FIG. 4 and Table 6; $p<0.05$). These results indicate that the native form of CTIP2 (CTIP2) is more relevant to the aggressiveness of HNSCC tumors and is involved in the progression of HNSCC.

CTIP2 is widely expressed in normal mouse (Golonzhka, et al., (2007) *Gene Expr Patterns* 7:754-760) and human epidermis (Ganguli et al., (2000) *EMBO J.* 19(19):5135-47.). As described herein, overexpresson of CTIP2 in HNSCC was demonstrated by IHC and QRT-PCR analysis. By designing primer specific for each form, it was possible to distinguish the expression pattern of two forms of CTIP2 in progression of HNSCC. Although $CTIP2_L$ is overexpressed in HNSCC, the native form is more (CTIP2) relevant to the disease progression.

Thus, as described herein, CTIP2 is over-expressed in head and neck squamous cell carcinomas, and CTIP2 expression corresponds to the degree of differentiation status of these tumors.

TABLE 6

Correlation between $CTIP2_L$ and CTIP2 mRNA expression levels and clinicopathological characteristics in HNSCC

| | Total | $CTIP2_L$ | CTIP2 |
|---|---|---|---|
| All cases | 28 | p value | |
| Tumor | | | |
| Differentiation | t test | 0.734 | 0.0439 |
| Well-Moderately | 18 | | |
| Poor-Undifferentiated | 10 | | |
| Tumor location | 1 way anova | 0.0716 | 0.2476 |
| Hypopharynx | 8 | | |
| Oral cavity | 10 | | |
| Oropharynx | 6 | | |
| Larynx | 4 | | |
| T Stage | t test | 0.8394 | 0.5511 |
| T1-T2 | 19 | | |
| T3-T4 | 9 | | |
| N Stage | t test | 0.6697 | 0.9862 |
| N0 | 13 | | |
| N+ | 15 | | |
| Clinical Stage | t test | 0.6737 | 0.3217 |
| I-II | 9 | | |
| III-IV | 19 | | |

Example 3

Additional Materials and Methods

This Example provides general materials and methods that were used for carrying out the experiments described below in Examples 4-7. Although specific procedures are described, one of skill in the art will recognize that other methods can be substituted.

Tissue Samples

Paraffin embedded tissue sections from 40 different head and neck tumors were obtained for immunohistochemistry, after informed consent from patients undergoing surgery as a primary treatment without previous radiation or chemotherapy treatment. Additionally, cDNA samples from 28 head and neck tumors, and 10 normal uvula cDNA samples were obtained from patients surgically treated for head and neck cancer that were at least two centimeters away from the tumor lesion. Tumors were classified according to TNM stage (tumor, node, metastasis) based on the UICC criteria (Sobin and Wittekind, 1997, in "TNM classification of malignant tumors, New York, Wiley-Liss, Inc.). Histopathological differentiation status was defined depending on the degree of keratin pearl formation, keratinization, overall resemblance to normal squamous epithelium, according to World Health Organization (WHO) criteria (Histological typing of upper respiratory tract tumors. Shanmugaratnam and Sobin (eds.). International Histological Classification of Tumors, 1978, Vol. 19. Springer-Verlag, Geneva.

Histopathological Features of HNSCC

Legends for tissue differentiation status:
1: well-differentiated
2: moderately-differentiated
3: poorly-differentiated (poorly differentiated tumors are the less differentiated squamous cell carcinomas.
4: undifferentiated (correspond to epithelial neoplasms without evidence of squamous or glandular differentiation).

T Size
1=T1, Tumor 2 cm. or less in greatest dimension
2=T2, Tumor greater than 2 cm. and less than 4 cm.
3=T3, Tumor greater than 4 cm.
4=T4, Tumor invades adjacent structures Tumor Staging
Stage I: T1N1M0
Stage II: T2N0M0
Stage III: T3N0M0, T1, T2, T3, N1M0
Stage IV: T4N0, N1M0, any T, N2, N3, M0, any T, any N, M Immunohistochemistry Formalin-fixed and paraffin-embedded HNSCC sections were used for immunohistochemistry. The sections were deparaffinized in xylene, dehydrated through graded alcohols, and placed in 0.1% hydrogen peroxide to quench any endogenous peroxidase activity. A 5-minute, 750 Watt microwave pretreatment in citrate buffer (pH 6.0) was repeated 4 times and followed by treatment with 10% normal rabbit serum for 30 minutes to block nonspecific antibody binding. The slides were then incubated with a rat CTIP2 monoclonal antibody, 1/300 dilution (Abcam product number 18465; clone 25B6) in a humid chamber at 4° C. overnight.

Secondary staining was carried out with a biotin-labeled rabbit anti-rat antibody 1/500 dilution for CTIP2 (Jackson Immuno Research Laboratories, INC, catalogue number: 112-065-143) for 2 hours at 37° C., followed by incubation with a streptavidin-biotin horseradish peroxidase complex (Vector Laboratories, catalog number: SA-5704). The reaction products were visualized by immersing the slides in freshly prepared diaminobenzidine solution (Vector: peroxide substrate kit, SK-4100) for 10 minutes and counterstaining with Mayer hematoxylin before dehydration and mounting.

CTIP2 expression was analyzed by comparing staining intensities between each tissue sample with and without addition of primary antibody. Several staining intensity experiments were conducted, each produced comparable results. Staining intensities for each section were as follows: 0, no staining; 1, weak staining; 2, moderate staining; 3, strong staining. A tumor was considered CTIP2 positive if more than 10% of the tumor cells demonstrated positive nuclear staining.

For immunofluorescence co-staining experiments, paraffin sections were rehydrated as described above and process as described by Golonzhka et al., 2007. The slides were incubated overnight in a humidified chamber with CTIP2 and BMI1 (Abcam: ab14389, 1/100), cytokeratin 10 (abcam: ab9026, 1/100) and Ki-67 (abcam: ab15580, 1/200) primary antibodies. Primary antibody incubation was followed by three washes with PBST and incubation with a fluorescently-labeled Cy2 (1:250) or Cy3 (1:500) (Jackson Immuno Research) secondary antibody for 2 hours. Nuclei were counterstained with DAPI. Sections were then rinsed with PBST, dehydrated through sequential washes in 50%, 70%, 95%, and 100% ethanol and then cleared in xylene. Slides were mounted with DPX mounting media and allowed to dry overnight. Images were captured at 40× magnification using a Leica DMRA Fluorescent Microscope and Hamamatsu Digital camera. Images were process using Open-Lab software and adobe Photoshop.

Cell Culture and Western Blotting

Cells were freshly thawed, cultured in their respective medium using the 3T3 protocol. When the cells reached 75%-80% confluency the medium was changed and the cells were harvested the next day and lysed in Laemmli buffer containing a protease inhibitor cocktail (Complete; Roche), 5 mM Dithiothreitol and boiled. The whole-cell extracts (20 μg protein) were subjected to SDS-PAGE and electro-blotted to nitrocellulose membranes. The membranes were blocked in 5% non-fat dry milk in 10 mM Tris-HCl, pH 7.8, 150 mM NaCl, 0.1% Tween 20, and incubated overnight with the rat monoclonal 25B6 to CTIP2 diluted 1/1000 in the blocking buffer and developed using Super Signal West Pico Chemiluminescent Substrate (Thermo Scientific Pierce).

Cell Lines

The following is a list of cell lines used in the proceeding examples. One of ordinary skill in the art will appreciate that other cell lines can be analyzed using the methods disclosed.

GM 193: lymphoblast, normal EBV transformed (NIGMS Human Genetic Mutant Cell Repository)

HUVEC: umbilical cord, endothelium, normal (ATCC CRL-1730)

GM 3348: skin, normal fibroblast (NIGMS)

HS677Tg: fibroblasts, tongue, normal (ATCC CRL-7408)

Hek-a: primary human epidermal keratinocytes from adult skin (HEKa, SKU# C-005-5C, Cascade)

Hacat: spontaneously immortalized non-tumorigenic human skin keratinocytes (IGBMC cell culture service, DKFZ).

SCC4: human squamous cell carcinoma, tongue (ATCC CRL-1624)

Cal 27: squamous cell carcinoma, tongue (IGBMC cell culture service, Dr. Merlin)

SCC25: human squamous cell carcinoma, tongue (ATCC CRL-1628)

SCC15: human squamous cell carcinoma, tongue (ATCC CRL-1623)

SCC9: human squamous cell carcinoma, tongue (ATCC CRL-1629)

CAL33: tongue cancer, elevated EGFR, contact inhibited tongue cancer (IGBMC Cell Culture Service, Dr. Merlin)

KB: epidermoid carcinoma, mouth (IGBMC cell culture service)

HSC2: human squamous cell carcinoma, oral (IGBMC cell culture service)

A253: epidermoid carcinoma, submaxillary salivary gland, (ATCC HTB-41)

HAN HN2: head and neck tumor (IGBMC cell culture service)

RPMI 2650: human squamous cell carcinoma, nasal septum, quasi-diploid (ATCC CCL-30)

Det 562: human epithelial carcinoma, pharynx, metastatic (ATCC CRL-7919)

Fadu: human squamous cell carcinoma, pharynx, primary tumorigenic (IGBMC cell culture service, Dr. Merlin)

Hep-2: epidermoid carcinoma, larynx (ATCC CCL-23)

MCF7: human Caucasian breast adenocarcinoma (ATCC HTB-22)

MCF10A: epithelial cell line, mammary gland, non-tumorigenic (ATCC CRL-10317).

Quantitative Real Time PCR (QRT-PCR)

Reverse transcription was performed as described previously (Seghatoleslam et al., Biochem. Biophys. Res. Commun., 339: 422-429, 2006). Briefly, reverse transcription was performed using 1 µg total RNA, random primers, and the superscript II TR-PCR system (Life Technologies). QRT-PCR was performed on 1/50 dilutions of the cDNA samples using SYBR Green Supermix (Qiagen) in an Applied Biosystems 7500 RT-PCR system as described (Indra et al., Dev. Biol., 285:28-37, 2005). All reactions were performed in triplicate. Melting curve analysis was performed to ensure the specificity of QRT-PCR. Primer sets used to test the expression of the two forms of CTIP2 were designed using Primer3 Software. Primers used in mouse mBmi1 were as described (Nowak et al., Nucleic Acids Research, 34:1745-1754, 2006). Data analysis was performed using the 2-ΔΔCt method described previously (Li et al., Clin. Cancer Res., 10: 8442-8450, 2004). Ribosomal phosphor-protein PO(RPLPO) and HPRT was used as reference genes. QRT-PCT based gene expression values between the groups were compared by t-test or 1 way ANOVA.

Primers for Real Time qRT-PCR

```
CTIP2_L (hCTIP2 E2-E3):
                                    (SEQ ID NO: 1)
(F) 5'-ATCTGTCCCAAGCAGGAGAA-3';

(SEQ ID NO: 2)
(R) 5'-GTCTGACCCTCACCCTGAGT-3'.

CTIP2 (hCTIP2 E2-E4):
                                    (SEQ ID NO: 3)
(f) 5'-AGCAGGAGAACATTGCAGGTA-3';

(SEQ ID NO: 4)
(R) 5'-GGAAATTCATGAGCGGGACT-3'.
```

Statistical Analysis

Positive cells for CTIP2, BMI1 and Ki-67 were determined by percent staining of cells with monoclonal antibody to CTIP2. The mean and standard error of QRT-PCR data among different samples was calculated, and the difference between the samples was determined by either t test or 1 way ANOVA. P values of $p<0.05$ were considered significant. Data are presented as mean±SEM.

The numbers of CTIP2, BMI1 and Ki-67 positive cells were counted and the total number of cells in the epidermis was used to calculate the percentages of positive cells. The analyses of CTIP2 expression were independently performed by two investigators.

Example 4

CTIP2 is a Marker of Tumor Differentiation Status

This example describes methods used to show CTIP2 expression levels in HNSCC samples and tumor differentiation status.

Figure 5:
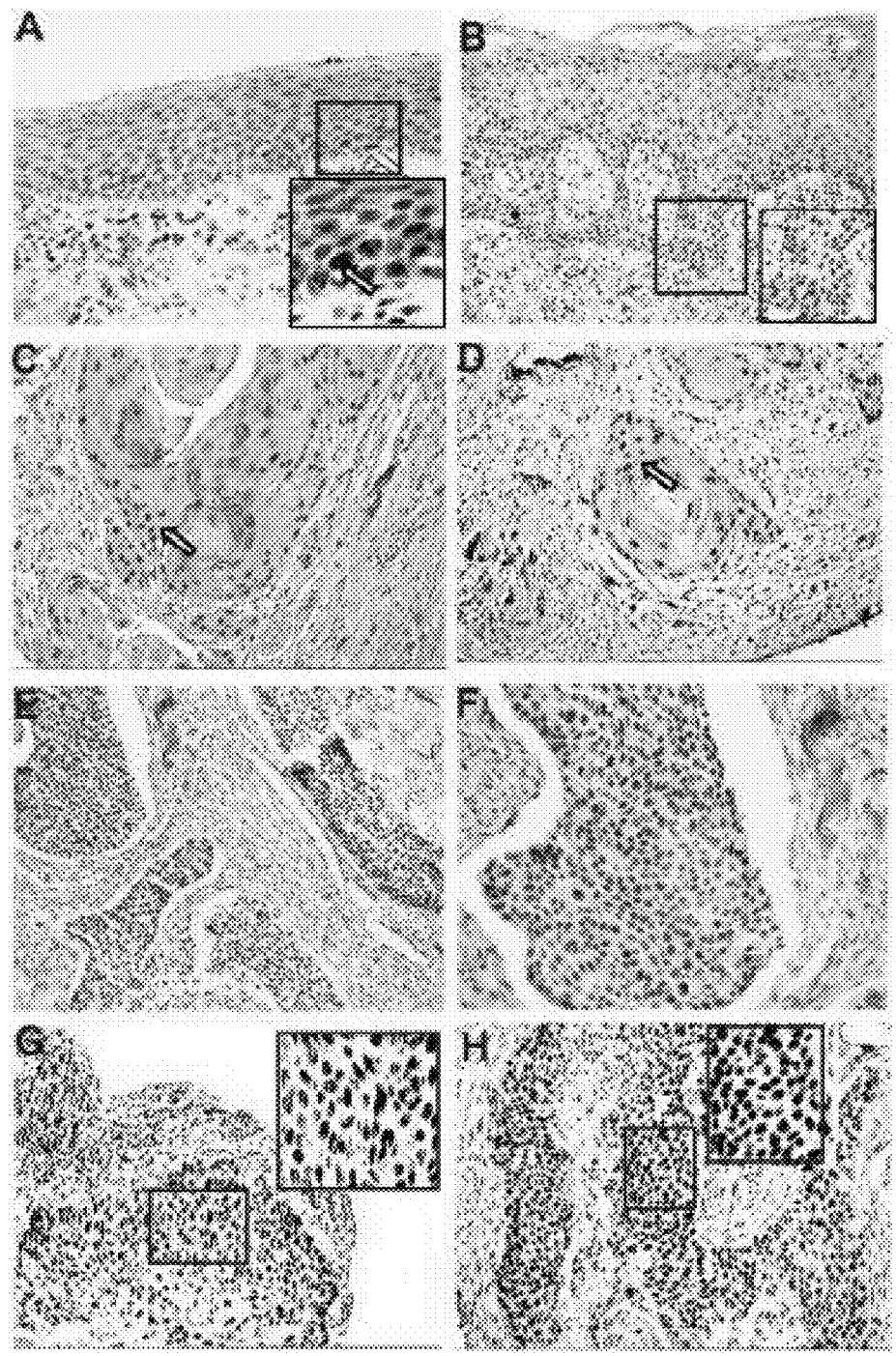
FIG. 5 includes several panels showing an immuno-histochemical (IHC) analysis of CTIP2 in HNSCC.

Immunohistochemical (IHC) Analyses of CTIP2 in Human Head and Neck Squamous Cell Cancers IHC staining was performed on paraffin embedded sections of head and neck tumors (n=40) and normal samples (n=12) using high heat antigen retrieval technique and a previously described CTIP2 antibody (Golonzhka et al., Gene Expr. Patterns., 7:754-60, 2007; Golonzhka et al., J. Invest. Dermatol., 129:1459-70, 2008). Positive staining for CTIP2 was observed to be exclusively nuclear. Negative control on sections stained without primary antibody or on skin sections from CTIP2 null mice confirmed no staining. In tumor adjacent normal epithelium, CTIP2 was expressed exclusively by keratinocytes of the basal layer and no expression was detected in cells of the spinous cell layer or granular layer (see Arrows of FIG. 5A and magnified inset). In dysplasia samples, CTIP2 expression was stronger compared to normal epithelium. Additionally, CTIP2 expression was determined to extend to the spinous cell layers (FIG. 5B and magnified inset). In well differentiated tumors, CTIP2 staining was observed in the outer layer of the keratinized horn-pearls clusters (FIGS. 5C and 5D). Stronger and homogeneous expression of CTIP2 was observed in moderately and/or poorly differentiated tumors (FIGS. 5E-5H and magnified insets) as compared to the well differentiated tumors (FIGS. 5C and 5D).

The intensities of CTIP2 staining (0-3) (as described in Examples 1 and 3) between the adjacent normal, dysplasia and different histological grades of head and neck tumors were compared (FIG. 2A and FIG. 2B). Out of the 40 different tumor samples analyzed, 12 of them had adjacent normal epithelium and 4 of them had dysplasia. Compared to normal epithelium, CTIP2 expression was strongly and significantly up-regulated in HNSCC samples ($p<0.05$) (FIG. 2A). The strongest intensity of CTIP2 staining (level 3) was observed in 11% of well differentiated tumors, 25% of the moderately differentiated tumors, and in 58% of the poorly differentiated tumors compared to no staining of this intensity in adjacent normal epithelium (FIG. 1, FIG. 5, FIG. 2A, FIG. 2B and Table 7).

TABLE 7

Staining intensities and percent positivity in normal epithelium and in HNSCC.

| Tumor differentiation | n* | Staining Intensities | | | |
|---|---|---|---|---|---|
| | | 0 | 1 | 2 | 3 |
| Adjacent Normal | 12 | 2 | 10 | 0 | 0 |
| Dysplasia | 4 | 0 | 1 | 2 | 1 |
| HNSCC-Well | 9 | 2(23) | 3(33) | 4(44) | 0(0) |
| HNSCC-Moderately | 12 | 2(17) | 4(33) | 3(25) | 3(25) |
| HNSCC-Poor | 19 | 2(10) | 3(16) | 3(16) | 11(58) |

TABLE 7-continued

Staining intensities and percent positivity in normal epithelium and in HNSCC.

| | | Percent positivity | | | |
|---|---|---|---|---|---|
| | n | 0-25 | 25-50 | 50-75 | 100 |
| Tumor differentiation | | | | | |
| Adjacent Normal | 12 | 12 | 0 | 0 | 0 |
| Well | 9 | 6 | 3 | 0 | 0 |
| Moderately | 12 | 4 | 6 | 2 | 0 |
| Poor | 19 | 5 | 6 | 8 | 0 |
| Tumor Stage | | | | | |
| Stage I-II | 22 | 14 | 6 | 2 | |
| Stage III-IV | 18 | 5 | 6 | 7 | 0 |

In brackets are the percentages of specific tumor types.

Overall, an increase in the intensity of CTIP2 expression with the progression of carcinoma was determined in all of the samples analyzed. Thus, these IHC results demonstrate that CTIP2 expression is elevated in HNSCC, and that CTIP2 expression is linked to poor differentiation status of the tumor.

Example 5

CTIP2 and BMI1 as Markers of Squamous Cell Carcinoma

This example describes CTIP2 expression and BMI1 expression in HNSCC samples and the correlation between CTIP2 and BMI1 expression levels and disease state, as well as the use of CTIP2 and BMI1 expression as a marker for HNSCC.

Figures 6A, 6B:
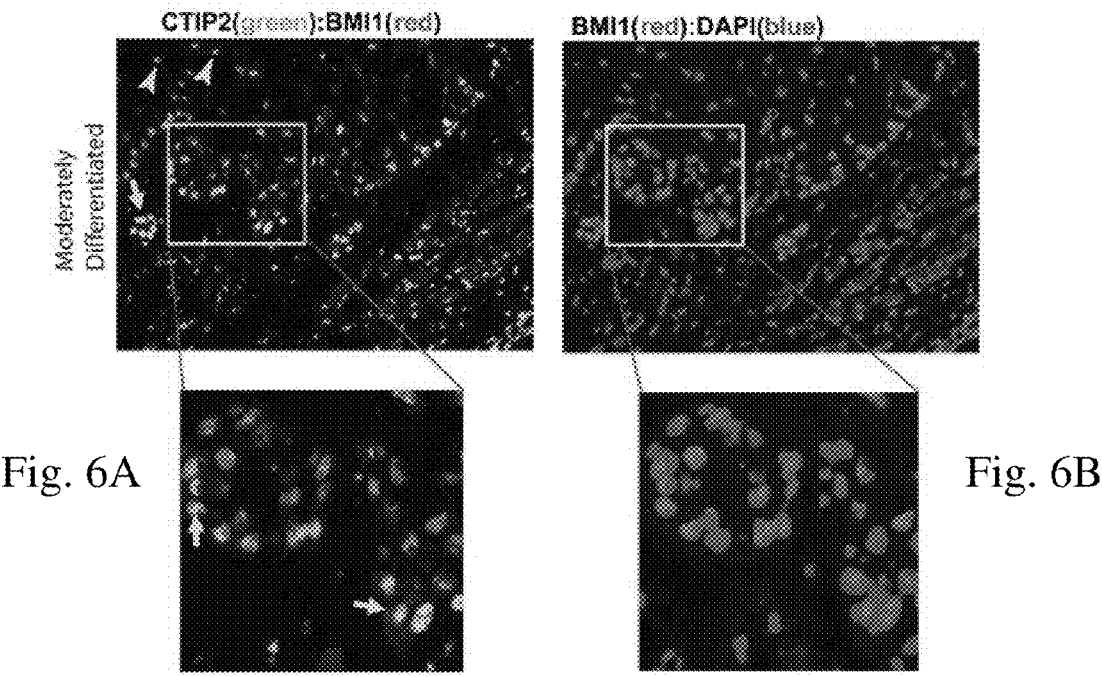
FIG. 6A is an immunological image of a moderately differentiated head and neck tumor co-stained with CTIP2 and BMI1.
FIG. 6B is an immunological image of the same tumor as provided in FIG. 6A, however the tumor is co-stained with BMI1 and DAPI.
Figure 9:
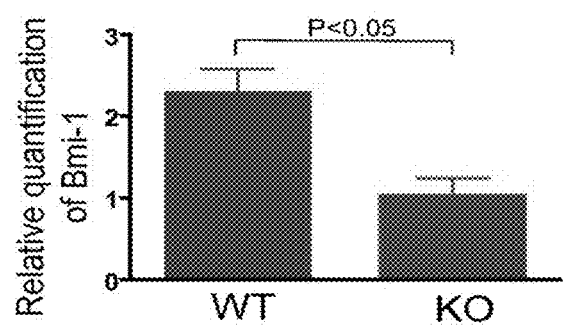
FIG. 9 shows expression of mouse BMI1 in CTIP2 mutant embryonic skin as determined by QRT-PCR.

Immunohistochemical (IHC) Analyses of CTIP2 and BMI1 in Human Head and Neck Squamous Cell Cancers Several reports have disclosed that polycomb group transcription factor, BMI1, is important for the self renewal of hematopoietic, neuronal stem cells as well as cancer stem/progenitor cells. In order to evaluate the role of CTIP2 in self renewal of tumor initiation and/or cancer stem cells in HSNCC, CTIP2 and BMI1 were immunofluorescently co-stained in well, moderately and poorly differentiated tumors. Staining of BMI1 was observed mostly in the basal cell layer and decreased towards the outer cell layers. In well and moderate to poorly differentiated tumors, the majority of BMI1 cells showed strong nuclear co-localization of CTIP2 and BMI1 proteins (FIGS. 6A and 6B). Some of the cancer cells were stained singularly positive for CTIP2 (CTIP2+/BMI1−) (FIG. 6A, inset). Interestingly, QRT-PCR performed on CTIP2 mutant mice skin, utilizing mouse specific Bmi1 primers, showed significant down regulation of Bmi1 expression, suggesting a possible regulation of the Bmi1 gene by CTIP2 (FIG. 9).

Furthermore, promoter analyses of the mouse and human BMI1 gene revealed the presence of several putative CTIP2 binding sites in the proximal and distal promoter region. The results support the existence of distinct subsets of cancer cells which express CTIP2 and demonstrate that CTIP2 and BMI1 co-labeling can be used to identify tumor initiating cancer stem cells (CSC).

Example 6

Expression of CTIP2 in Human Cell Lines

CTIP2 protein expression in human cell lines was detected by western blotting a panel of human cell lines that included normal, HNSCC and other types of carcinomas (as disclosed in Example 3).

Figure 6C:
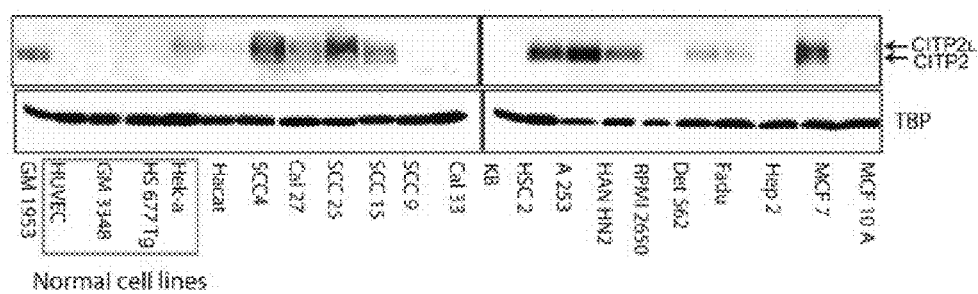
FIG. 6C is an image of a western blot showing expression of CTIP2 in various normal cell lines, head and neck squamous cell cancer lines and other types of carcinomas.

Weak expression of CTIP2 was detected in primary human epidermal keratinocytes (Hek-a) and in spontaneously immortalized non-tumorigenic human skin keratinocytes (Hacat) (FIG. 6C).

CTIP2 expression was undetectable in some normal cell lines from umbilical cord endothelium (HUVEC), skin and tongue fibroblasts (GM 3348 and HS677Tg). In contrast, high levels of CTIP2 expression were detected in HNSCC cell lines (SCC4, SCC25, HSC2, HAN HN2) and in other carcinoma cell lines such as epidermoid carcinoma from submaxillary salivary gland (A253) and breast carcinoma (MCF 7) (FIG. 6C).

Surprisingly, weaker expression was detected in some HNSCC cell lines, such as Det562 and Fadu, and no expression was detected in cell line RPMI 2650. In most cases, CTIP2 expression levels were lower than the internal control—TATA box binding protein (TBP)(see lower panel of FIG. 6C). The results demonstrate that the majority of HNSCC cell lines analyzed herein were observed to have increased expression of CTIP2 as compared to a normal (non-cancerous) cell line.

Example 7

Co-Labeling of CTIP2 with a Proliferation and Differentiation Marker

To confirm CTIP2 was linked to the proliferation and differentiation of SCC, an immunofluorescence method was used to co-label CTIP2 with a proliferation (Ki-67) and differentiation (cytokeratin 10 (K10)) marker in HNSCC samples.

Figure 7:
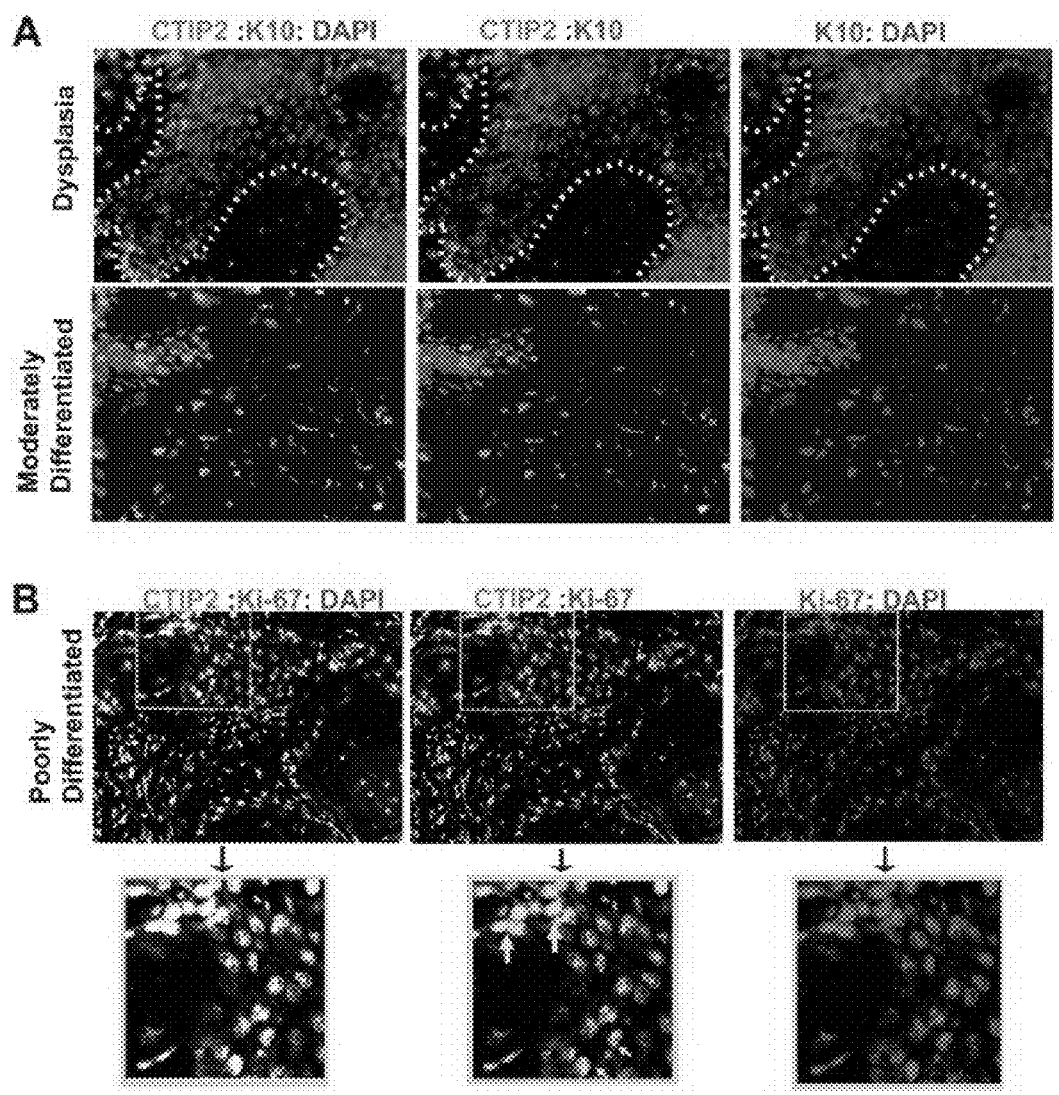
FIG. 7 is an immunohistochemical image of various tissue sections co-stained with CTIP2, Ki67, K10 or DAPI.

Cytoplasmic expression of K10 was determined to occur in clusters or in scattered areas of dysplastic samples and also in tumors with well or moderately differentiated status (FIG. 7A). In the dysplastic samples, most of the supra basal layer cells that were positive for CTIP2 also expressed K10.

In moderately differentiated tumor samples with low levels of CTIP2 expression, K10 was expressed in clusters (FIG. 7A). It was also determined that some of the CTIP2 positive cells also expressed K10.

In poorly differentiated tumors with less differentiation (less K10 positively), high levels of CTIP2 were observed that did not express K10. Using an analogous method, it was determined that CTIP2 can co-label with the proliferation marker Ki-67 in normal human skin and in eczematous skin (Ganguli-Indra et al., PLos One., doi: 10.1371/journal.pone.0005367, 2009). Utilizing the same cell line as provided in the above co-labeling experiment (HNSCC), most of the CTIP2 positive cells were found to be co-labeled with Ki-67 (FIG. 7B, see double arrow of inset).

The co-labeling results using K10 and Ki-67 disclose that CTIP2 expression is linked to tumor differentiation state and proliferation. Poorly differentiated tumors which are less differentiated, contain more proliferative cells, and hence have higher CTIP2 expression. The K10 and Ki-67 staining patterns confirm that CTIP2 is linked to differentiation status of the tumor. Less differentiated tumors (i.e., poorly differentiated tumors) express high CTIP2 levels with proliferative nature (as shown by co-labeling with Ki-67) and express low levels of K10.

Example 8

Expression of CTIP2 Transcripts in Human HNSCC

To establish which isoform(s) of CTIP2 are relevant to HNSCC disease progression; the known CTIP2 isoforms were evaluated by quantitative real time PCR (QRT-PCR). Using QRT-PCR two human CTIP2 spliced transcript variants, which encode distinct isoforms were evaluated (FIG. 8).

As used herein, ($CTIP2_L$) refers to CTIP2 with all 4 exons. In contrast, CTIP2 refers to the variant lacking exon 3 which is the native or normal form (FIG. 8), and the variant lacking both exon 2 and exon 3 is referred to as CTIP2 short.

QRT-PCR was performed for $CTIP2_L$ and CTIP2, on RNA extracted from 28 different HNSCC samples and amplifications were normalized using RPLPO as an internal control. 10 normal uvulas were included to compare the expression levels of the normal transcripts to the 28 HNSCC samples. To distinguish between the two isoforms, specific primers from exon 2 and exon 3 for $CTIP2_L$, and exon 2 and overlapping exons 2 and 4 for CTIP2 were designed (FIG. 8).

Figure 10:
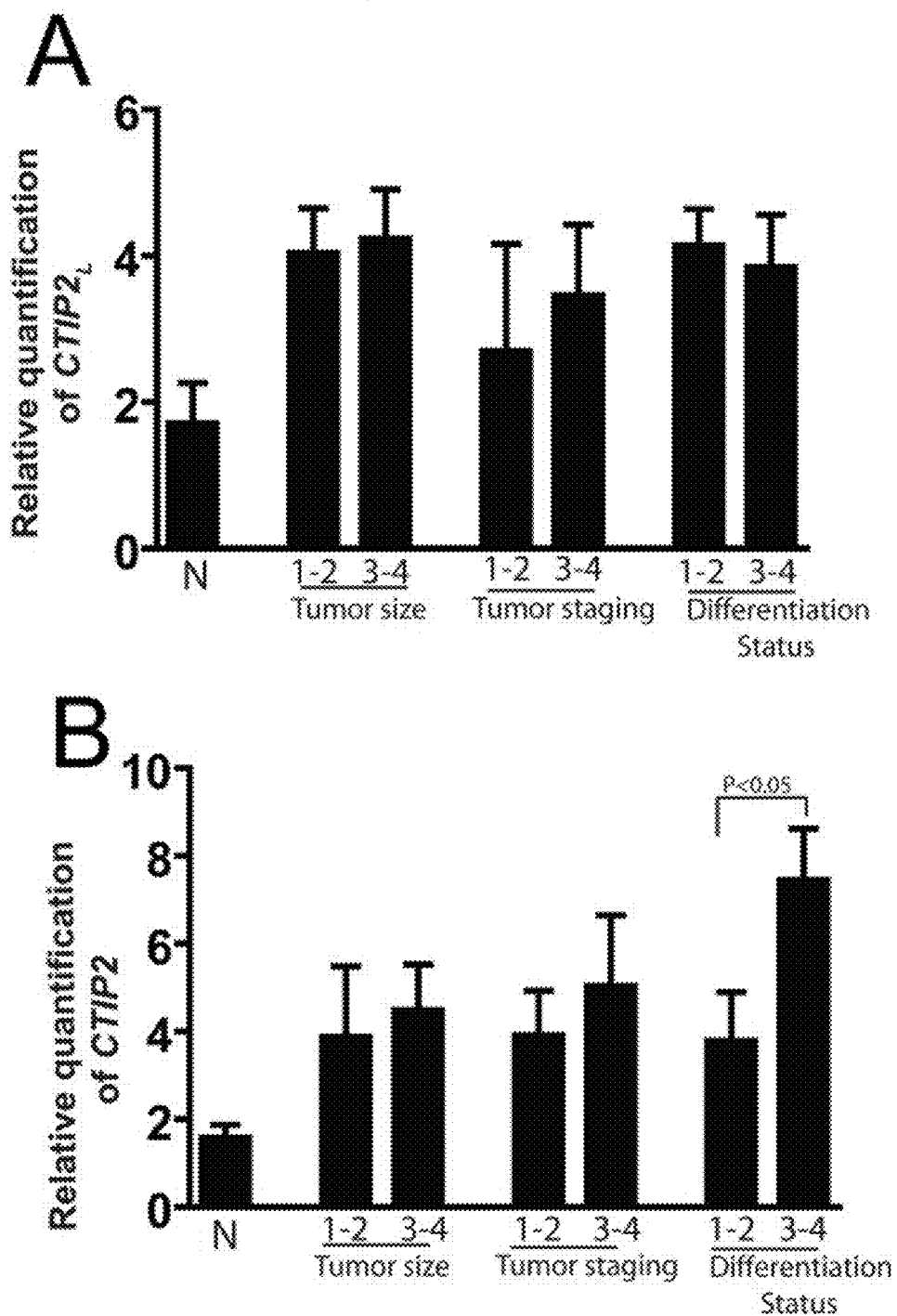
FIG. 10 includes two panels showing expression of CTIP2 long form ($CTIP2_L$) and CTIP2 by QRT-PCR in HNSCC.

The samples based on different tumor sizes (T size), Tumor staging (T staging) and differentiation status (see Example 1) were divided into early cancer (1-2) and late cancer (3-4), respectively. A significant number of samples with normal to high mRNA expression of $CTIP2_L$ were observed among patients with T1-T4 tumor size and with well, moderate to poor differentiation status, and regional metastasis. However, statistical studies showed no statistical significance of any correlation between mRNA expression of $CTIP2_L$ and any of the clinicopathological parameters (Table 8 and FIG. 10A).

On the contrary, there was a significant correlation of higher CTIP2 expression with a poorer histological grade of the tumor, and a trend was noted in a relationship between expression and advanced tumor (T size) or Tumor staging (Table 8 and FIG. 10B)($p<0.05$). The results show that although both forms of CTIP2 are elevated in HNSCC only CTIP2 is linked to the poor differentiation status of the tumor.

TABLE 8

Correlation between CTIP2 mRNA expression levels and clinicopathological characteristics in HNSCC
Total

| | Total | $CTIP2_L$ | CTIP2 |
|---|---|---|---|
| All cases | 28 | P value | P value |
| Tumor differentiation status | t test | 0.734 | 0.0439 |
| Well-Moderately | 18 | | |
| Poor-Undifferentiated | 10 | | |
| Tumor location | 1 way anova | 0.0716 | 0.2476 |
| Hypopharynx | 8 | | |
| Oral cavity | 10 | | |
| Oropharynx | 6 | | |
| larynx | 4 | | |
| Tumor size | t test | 0.8394 | 0.5511 |
| T1-T2 | 19 | | |
| T3-T4 | 9 | | |
| N Stage | t test | 0.6697 | 0.9862 |
| N0 | 13 | | |
| N+ | 15 | | |
| Tumor Staging | t test | 0.6737 | 0.3217 |
| I-II | 9 | | |
| III-IV | 19 | | |

Statistical analysis was performed as described in Example 3.

In view of the many possible embodiments to which the principles of the disclosure can be applied, it should be recognized that the illustrated examples are only examples of the disclosure and should not be taken as limiting the scope of the invention. Rather, the scope of the invention is defined by the following claims. We therefore claim as our invention all that comes within the scope and spirit of these claims.

The invention claimed is:

1. A method for detecting head and neck squamous cell carcinoma in a subject comprising: measuring CTIP2 and/or CTIP2$_L$ expression in a sample of head and neck tissue obtained from the subject, comparing the level of CTIP2 and/or CTIP2$_L$ expression in the sample to the level of expression of CTIP and/or CTIP2$_L$ in a non-cancerous, non-dysplastic head and neck tissue sample, and determining that there is an indication of the presence of head and neck squamous cell carcinoma in the subject when there is an increase in the level of expression of CTIP2 and/or CTIP2$_L$ in the sample obtained from the subject relative to the level of expression of CTIP2 and/or CTIP2$_L$ in the non-cancerous, non-dysplastic head and neck tissue sample.

2. The method of claim 1, wherein measuring CTIP2 expression comprises measuring CTIP2 and/or CTIP2$_L$ protein expression.

3. The method of claim 2, wherein measuring CTIP2 and/or CTIP2$_L$ protein expression comprises: contacting the sample with a CTIP2- and/or CTIP2$_L$-specific antibody under conditions sufficient for binding of the antibody to CTIP2 proteins in the sample, thereby forming CTIP2- and/or CTIP2$_L$-antibody complexes; and detecting the CTIP2- and/or CTIP2$_L$ antibody complexes.

4. The method of claim 3, wherein measuring the CTIP2-antibody complexes comprises: contacting the CTIP2- and/or CTIP2$_L$-antibody complexes with a secondary antibody comprising a label under conditions sufficient for binding of the secondary antibody to CTIP2-antibody complexes, thereby forming labeled-CTIP2- and/or CTIP2$_L$-antibody complexes; and detecting the label.

5. The method of claim 1, wherein measuring CTIP2 and/or CTIP2$_L$ expression comprises detecting CTIP2 and/or CTIP2$_L$ nucleic acid molecule expression.

6. The method of claim 5, wherein measuring CTIP2 nucleic acid molecule expression comprises detecting CTIP2 and/or CTIP2$_L$ mRNA expression.

7. The method of claim 1, further comprising comparing the level of CTIP2 and/or CTIP2$_L$ expression in the sample to the level of expression of CTIP and/or CTIP2$_L$ in a tissue sample containing head and neck squamous cell carcinoma, and determining that there is an indication of the presence of head and neck squamous cell carcinoma in the subject when the level of expression of in the sample obtained from the subject is substantially similar to the level of expression of CTIP2 and/or CTIP2$_L$ in the tissue sample containing head and neck squamous cell carcinoma.

8. The method of claim 1, wherein said increase in the level of expression of CTIP2 or CTIP2$_L$ in the sample obtained from the subject relative to the level of expression of CTIP2 or CTIP2$_L$ in the non-cancerous, non-dysplastic head and neck tissue sample is at least 2-fold.

* * * * *

UNITED STATES PATENT AND TRADEMARK OFFICE
CERTIFICATE OF CORRECTION

PATENT NO. : 8,071,815 B2  
APPLICATION NO. : 12/505437  
DATED : December 6, 2011  
INVENTOR(S) : Indra et al.

Page 1 of 1

It is certified that error appears in the above-identified patent and that said Letters Patent is hereby corrected as shown below:

In the Claims:

Column 53, line 43, claim 3, "$CTIP2_L$ antibody" should be --$CTIP2_L$-antibody--.

Column 54, line 36, claim 7, "of in" should be --in--.

Signed and Sealed this  
Tenth Day of July, 2012

David J. Kappos  
*Director of the United States Patent and Trademark Office*

UNITED STATES PATENT AND TRADEMARK OFFICE
CERTIFICATE OF CORRECTION

PATENT NO. : 8,071,815 B2  Page 1 of 1
APPLICATION NO. : 12/505437
DATED : December 6, 2011
INVENTOR(S) : Indra et al.

It is certified that error appears in the above-identified patent and that said Letters Patent is hereby corrected as shown below:

In the Claims:

Column 53, lines 40-41, claim 3, "CTIP2 proteins" should be --CTIP2 and/or $CTIP2_L$ proteins--.

Column 54, line 32, claim 7, "CTIP" should be --CTIP2--.

Column 54, line 36, claim 7, "of in" should be --of CTIP2 and/or $CTIP2_L$ in--.

Signed and Sealed this
Seventh Day of August, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,071,815 B2 | Page 1 of 1 |
| APPLICATION NO. | : 12/505437 | |
| DATED | : December 6, 2011 | |
| INVENTOR(S) | : Indra et al. | |

It is certified that error appears in the above-identified patent and that said Letters Patent is hereby corrected as shown below:

In the Specification:

The following heading and paragraph should be added at column 1, line 19:

--ACKNOWLEDGMENT OF GOVERNMENT SUPPORT

This invention was made with government support under R01 AR056008 awarded by National Institutes of Health. The government has certain rights in the invention.--

Signed and Sealed this
Fifteenth Day of March, 2016

Michelle K. Lee
*Director of the United States Patent and Trademark Office*